United States Patent
Lachia et al.

(10) Patent No.: US 10,392,348 B2
(45) Date of Patent: Aug. 27, 2019

(54) 2-OXO-3,4-DIHYDROQUINOLINE COMPOUNDS AS PLANT GROWTH REGULATORS

(71) Applicant: Syngenta Participations AG, Basel (CH)

(72) Inventors: Mathilde Denise Lachia, Stein (CH); Sebastian Volker Wendeborn, Stein (CH); Pierre Joseph Marcel Jung, Stein (CH); Davide Sabbadin, Stein (CH); Olivier Loiseleur, Stein (CH); Andreas Beck, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/548,141

(22) PCT Filed: Feb. 5, 2016

(86) PCT No.: PCT/EP2016/052492
§ 371 (c)(1),
(2) Date: Aug. 2, 2017

(87) PCT Pub. No.: WO2016/128317
PCT Pub. Date: Aug. 18, 2016

(65) Prior Publication Data
US 2018/0044297 A1    Feb. 15, 2018

(30) Foreign Application Priority Data

Feb. 9, 2015  (GB) .................................. 1502067.0
May 28, 2015 (GB) .................................. 1509129.1

(51) Int. Cl.
| | |
|---|---|
| *A01N 43/42* | (2006.01) |
| *C07D 401/04* | (2006.01) |
| *C07D 215/227* | (2006.01) |
| *A01P 13/02* | (2006.01) |
| *A01P 15/00* | (2006.01) |

(52) U.S. Cl.
CPC ......... *C07D 215/227* (2013.01); *A01N 43/42* (2013.01); *C07D 401/04* (2013.01)

(58) Field of Classification Search
CPC ... C07D 215/227; C07D 401/04; A01N 43/42
See application file for complete search history.

(56) References Cited

FOREIGN PATENT DOCUMENTS

| | | | |
|---|---|---|---|
| JP | 2009-51830 | * | 3/2009 |
| WO | 2013/148339 A1 | | 10/2013 |
| WO | 2014/210555 A1 | | 12/2014 |

OTHER PUBLICATIONS

Derwent abstract 2009-F84879 (abstracting JP 2009-51830), Mar. 2009.*
JPO abstract 2009051830, Mar. 2009.*
Partial machine translation of JP 2009-51830 (Mar. 2009).*
International Search Report for International Patent Application No. PCT/EP2016/052492 dated Mar. 15, 2016.
Written Opinion for International Patent Application No. PCT/EP2016/052492 dated Mar. 15, 2016.

* cited by examiner

*Primary Examiner* — John Pak
(74) *Attorney, Agent, or Firm* — Baker and Hostetler LLP; Toni-Junell Herbert

(57) ABSTRACT

The present invention relates to novel sulfonamide derivatives of formula (I), to processes and intermediates for preparing them, to plant growth regulator compositions comprising them and to methods of using them for controlling the growth of plants, improving plant tolerance to abiotic stress (including environmental and chemical stresses), inhibiting seed germination and/or safening a plant against phytotoxic effects of chemicals.

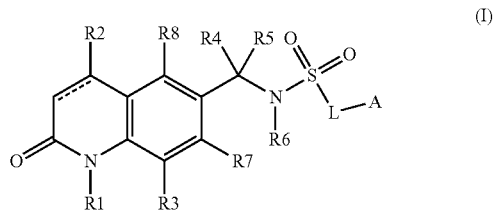

15 Claims, No Drawings

2-OXO-3,4-DIHYDROQUINOLINE COMPOUNDS AS PLANT GROWTH REGULATORS

RELATED APPLICATION INFORMATION

This application is a 371 of International Application No. PCT/EP2016/052492, filed 5 Feb. 2016, which claims priority to GB 1502067.0, filed 9 Feb. 2015, and GB 1509129.1, filed 28 May 2015, the contents of which are incorporated herein by reference herein.

The present invention relates to novel sulfonamide derivatives, to processes and intermediates for preparing them, to plant growth regulator compositions comprising them and to methods of using them for controlling the growth of plants, improving plant tolerance to abiotic stress (including environmental and chemical stresses), inhibiting seed germination and/or safening a plant against phytotoxic effects of chemicals.

Abscisic acid (ABA) is a plant hormone that plays a major role in plant growth, development and response to abiotic stress. ABA causes many of its cellular responses by binding to a soluble family of receptors called PYR/PYL proteins, which contain a ligand-binding pocket for ABA and other agonists. Direct application of ABA to plants has been shown to improve their water use efficiency. However, ABA is difficult and expensive to prepare and itself unstable to environmental conditions and therefor unsuitable for large scale agricultural applications. It is therefore desirable to search for ABA agonists that may be useful for improving plant tolerance to environment stress such as drought, inhibit seed germination, regulate plant growth and improve crop yield.

WO2013/148339 reported a new ABA agonist, quinabactin, which binds to the PYR/PRL receptor proteins and causes an abscisic acid response in vivo. Quinabactin has been shown to induce stomatal closure, suppress of water loss and promote drought tolerance.

There is a need to identify improved agonists of abscisic acid for improving plant growth and development, and plant tolerance to environmental stresses. The present invention relates to novel analogs of quinabactin that have improved properties. Benefits of the compounds of the present invention include enhanced tolerance to abiotic stress, improved inhibition of seed germination, better regulation of crop growth, improved crop yield, and/or improved physical properties resulting in better plant uptake, water solubility, chemical stability or physical stability.

According to the present invention, there is provided a compound of Formula (I)

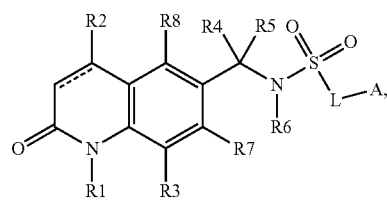

(I)

wherein:
R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$ alkenyl, $C_3$-$C_7$ alkynyl, aryl-$C_1$-$C_7$ alkyl, (3-6 membered heterocyclyl)-$C_1$-$C_7$ alkyl, phenyl, $C_3$-$C_5$ cycloalkyl and a 4-6 membered heterocyclyl, each optionally substituted with one to three Rx;

R2 is selected from the group consisting of hydrogen, cyano, $C_1$-$C_4$ alkyl, $C_1$-$C_4$ alkoxy, $C_1$-$C_4$ haloalkyl, $C_1$-$C_4$ haloalkoxy and $C_3$-$C_4$ cycloalkyl;

R3, R7 and R8 are independently selected from the group consisting of hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl;

R4 and R5 are independently selected from the group consisting of hydrogen, $C_1$-$C_4$ alkyl, $C_1$-$C_4$ haloalkyl and $C_3$-$C_4$ cycloalkyl;

or R4 and R5 can form, together with the atom or atoms they are directly attached to, a $C_3$-$C_4$ cycloalkyl or $C_4$ heterocyclyl;

R6 is selected from the group consisting of hydrogen, $C_1$-$C_4$ alkyl, $C_3$-$C_4$ alkenyl, $C_3$-$C_4$ alkynyl, and $C_1$-$C_3$ alkoxy-$C_1$-$C_4$-alkyl;

L is selected from the group consisting of a bond, a linear —$C_1$-$C_4$-alkyl chain, a linear —$C_2$-$C_4$-alkenyl chain, a linear —$C_2$-$C_4$-alkynyl chain, a linear —$C_1$-$C_4$-alkoxy chain whereby the oxygen atom is attached to A, a linear -amino-$C_1$-$C_4$-alkyl-chain whereby the nitrogen atom is attached to A, and a linear $C_1$-$C_2$alkyl-oxy-$C_1$-$C_2$alkyl chain, each optionally substituted with one to three halogen, cyano, $C_1$-$C_4$ alkyl, $C_1$-$C_4$ haloalkyl or $C_1$-$C_4$ alkoxy;

A is hydrogen, $C_1$-$C_7$ alkyl, $C_3$-$C_5$ cycloalkyl, 3-10 membered heterocyclyl or aryl, each optionally substituted with one to three Ry;

Rx is, independently of each other, selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl;

Ry is, independently of each other, selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkyloxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl which cycloalkyl is unsubstituted or substituted by one or more Rz; and Rz is independently selected from the group consisting of halogen, $C_1$-$C_4$-alkyl and $C_1$-$C_4$-haloalkyl;

wherein A is not butyl when either R4 or R5 is methyl;

and wherein R1 is not methyl when R2, R3, R4, R5, R6, R7 and R8 are each hydrogen;

or salts or N-oxides thereof.

The compounds of the present invention may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of the present invention.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups include $C_1$-$C_6$ alkyl, $C_1$-$C_4$ alkyl, and $C_1$-$C_3$ alkyl.

The term "alkenyl", as used herein, is an alkyl moiety having at least one carbon-carbon double bond, for example $C_2$-$C_6$ alkenyl. Specific examples include vinyl and allyl. The alkenyl moiety may be part of a larger group (such as alkenoxy, alkenoxycarbonyl, alkenylcarbonyl, alkyenlaminocarbonyl, dialkenylaminocarbonyl).

The term "acetoxy" refers to —OC(=O)CH$_3$.

The term "alkynyl", as used herein, is an alkyl moiety having at least one carbon-carbon triple bond, for example $C_2$-$C_6$ alkynyl. Specific examples include ethynyl and propargyl. The alkynyl moiety may be part of a larger group (such as alkynoxy, alkynoxycarbonyl, alkynylcarbonyl, alkynylaminocarbonyl, dialkynylaminocarbonyl).

Halogen is fluorine (F), chlorine (Cl), bromine (Br) or iodine (I).

Haloalkyl groups (either alone or as part of a larger group, such as haloalkoxy or haloalkylthio) are alkyl groups which are substituted with one or more of the same or different halogen atoms and are, for example, —CF$_3$, —CF$_2$Cl, —CH$_2$CF$_3$ or —CH$_2$CHF$_2$.

Hydroxyalkyl groups are alkyl groups which are substituted with one or more hydroxyl group and are, for example, —CH$_2$OH, —CH$_2$CH$_2$OH or —CH(OH)CH$_3$.

Alkoxyalkyl groups are an alkoxy group bonded to an alkyl (R—O—R), for example —(CH$_2$)$_r$O(CH$_2$)$_s$CH$_3$, wherein r is 1 to 6 and s is 1 to 5.

In the context of the present specification the term "aryl" refers to a ring system which may be mono-, bi- or tricyclic. Examples of such rings include phenyl, naphthalenyl, anthracenyl, indenyl or phenanthrenyl.

Unless otherwise indicated, alkenyl and alkynyl, on their own or as part of another substituent, may be straight or branched chain and may contain 2 to 6 carbon atoms, and where appropriate, may be in either the (E)- or (Z)-configuration. Examples include vinyl, allyl, ethynyl and propargyl.

Unless otherwise indicated, cycloalkyl may be mono- or bi-cyclic, may be optionally substituted by one or more $C_1$-$C_6$ alkyl groups, and contain 3 to 7 carbon atoms. Examples of cycloalkyl include cyclopropyl, 1-methylcyclopropyl, 2-methylcyclopropyl, cyclobutyl, cyclopentyl and cyclohexyl.

The term "heterocyclyl" refers to a ring system containing from one to four heteroatoms selected from N, O and S, wherein the nitrogen and sulphur atoms are optionally oxidized, and the nitrogen atom(s) are optionally quaternized. Heterocyclyl includes heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl. In addition, the term "heterocyclyl" includes heterocycloalkyl, a non-aromatic monocyclic or polycyclic ring comprising carbon and hydrogen atoms and at least one heteroatom selected from nitrogen, oxygen, and sulfur such asoxetanyl or thietanyl.

The term "heteroaryl" refers to an aromatic ring system containing from one to four heteroatoms selected from N, O, and S, wherein the nitrogen and sulfur atoms are optionally oxidized, and consisting either of a single ring or of two or more fused rings. Single rings may contain up to three heteroatoms, and bicyclic systems up to four heteroatoms, which will preferably be chosen from nitrogen, oxygen and sulfur. Examples of such groups include pyridyl, pyridazinyl, pyrimidinyl, pyrazinyl, furanyl, thienyl, oxazolyl, isoxazolyl, oxadiazolyl, thiazolyl, isothiazolyl, thiadiazolyl, pyrrolyl, pyrazolyl, imidazolyl, triazolyl and tetrazolyl.

Preferred values of R1, R2, R3, R4, R5, R6, R7, R8, L, A, Rx, Ry and Rz are, in any combination, as set out below.

Preferably R1 is selected from the group consisting of $C_1$-$C_6$ alkyl, $C_1$-$C_6$ haloalkyl, $C_3$-$C_5$ cycloalkyl-$C_1$-$C_6$ alkyl, $C_3$-$C_6$ alkenyl, $C_3$-$C_6$ alkynyl, phenyl and a 4-6 membered heterocyclyl, each optionally substituted with one to three Rx.

Preferably R1 is selected from the group consisting of $C_1$-$C_6$ alkyl, $C_1$-$C_6$ haloalkyl, $C_3$-$C_6$ alkenyl and $C_3$-$C_5$-cycloalkyl-$C_1$-$C_6$ alkyl. Preferably R1 is selected from the group consisting of $C_1$-$C_6$ alkyl, $C_3$-$C_5$ alkenyl, $C_3$-$C_5$-cycloalkyl-$C_1$-$C_2$ alkyl and $C_2$-$C_4$ haloalkyl. Preferably, R1 is ethyl, isopropyl, n-propyl, allyl, cyclopropyl-methyl or 2,2,2-trifluoro-ethyl. The alkyl chain may be branched or linear. In one embodiment R1 is methyl. In one embodiment R1 is ethyl. In one embodiment R1 is n-propyl or iso-propyl. In one embodiment R1 is n-butyl, iso-butyl, sec-butyl or tert-butyl. In one embodiment R1 is allyl, cyclopropyl-methyl or 2,2,2-trifluoro-ethyl.

Preferably R2 is selected from the group consisting of hydrogen, $C_1$-$C_4$ alkyl and $C_1$-$C_4$ alkoxy. Preferably R2 is selected from the group consisting of hydrogen and $C_1$-$C_4$ alkyl.

Preferably R3 is selected from the group consisting of hydrogen, halogen, cyano, $C_1$-$C_4$ alkyl and $C_1$-$C_4$ alkoxy. Preferably R3 is selected from the group consisting of hydrogen, halogen and $C_1$-$C_4$ alkyl.

Preferably each of R4 and R5 are independently selected from the group consisting of hydrogen and $C_1$-$C_4$ alkyl. Preferably each of R4 and R5 is independently hydrogen or methyl.

Preferably R6 is hydrogen.

Preferably each of R7 and R8 are independently selected from the group consisting of hydrogen, halogen, cyano, $C_1$-$C_4$ alkyl and $C_1$-$C_4$ alkoxy.

Preferably L is selected from the group consisting of a bond, a linear —$C_1$-$C_4$-alkyl chain, a linear —$C_2$-$C_4$-alkenyl chain, and a linear —$C_2$-$C_4$-alkynyl chain. In one embodiment, L is a bond. In one embodiment, L is a linear —$C_1$-$C_4$-alkyl chain. In one embodiment, L is a —$C_2$-$C_4$-alkenyl chain.

Preferably A is selected from the group consisting of $C_1$-$C_7$ alkyl, phenyl and 3-6 membered heteroaryl, each optionally substituted with one to three Ry. Preferably A is a 5-6 membered heteroaryl or phenyl, each optionally substituted with one to three Ry. Preferably A is phenyl optionally substituted with one to three substituents independently selected from the group consisting of halogen, cyano, $C_1$-$C_4$ alkyl, $C_1$-$C_4$ haloalkyl, $C_1$-$C_4$ haloalkoxy, $C_1$-$C_4$ haloalkylsulfanyl and $C_3$-$C_4$ cycloalkyl. In one embodiment, A is phenyl optionally substituted with one to three substituents independently selected from the group consisting of halogen, $C_1$-$C_4$ alkyl, $C_1$-$C_4$ haloalkyl and $C_1$-$C_4$ haloalkoxy. In one embodiment, A is phenyl. In one embodiment, A is a 5-6 membered heteroaryl selected from the group consisting of pyridyl, pyridazinyl, pyrimidinyl, pyrazinyl, furanyl, thienyl, oxazolyl, isoxazolyl, oxadiazolyl, thiazolyl, isothiazolyl, thiadiazolyl, pyrrolyl, pyrazolyl, imidazolyl, triazolyl and tetrazolyl. In one embodiment, A is thienyl optionally substituted with one to three substituents independently selected from the group consisting of halogen, $C_1$-$C_4$ alkyl, $C_1$-$C_4$ haloalkyl and $C_1$-$C_4$ haloalkoxy.

Preferably Rx is selected from the group consisting of halogen, $C_1$-$C_4$ alkyl, $C_1$-$C_4$ haloalkyl and $C_1$-$C_4$ alkoxy. Preferably Rx is selected from the group consisting of halogen and $C_1$-$C_4$ alkyl. In one embodiment, Rx is halogen. In a further embodiment, Rx is methyl. In a further embodiment, Rx is ethyl.

Preferably Ry is selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkoxy, $C_1$-$C_4$ haloalkylsulfanyl and $C_3$-$C_4$ cycloalkyl. Preferably, Ry is selected from the group consisting of halogen, $C_1$-$C_4$ haloalkyl and $C_1$-$C_4$ alkyl. In one embodiment, Ry is selected from the group consisting of cyano, methyl, ethyl, cyclopropyl, trifluoromethyl, difluoromethyl, trifluoromethyloxy, difluoromethyloxy and trifluoromethylsulfanyl. In one embodiment, each Ry is selected from the group consisting of halogen, cyano, methyl, ethyl, propyl, cyclopropyl and butyl. In a further embodiment, each Ry is selected from the group consisting of F, Cl, and Br. In one embodiment, Ry is fluoro. In another embodiment, Ry is difluoromethyl. In another embodiment, Ry is trifluoromethyl. In another embodiment, Ry is $C_1$-$C_4$ haloalkylsulfanyl.

Preferably Rz is selected from the group consisting of halogen and $C_1$-$C_4$-alkyl. In one embodiment, Rz is halogen.

In one embodiment of formula (I):
R1 is selected from the group consisting of $C_1$-$C_6$ alkyl, $C_3$-$C_5$-cycloalkyl-$C_1$-$C_6$ alkyl, $C_3$-$C_6$ alkenyl and $C_1$-$C_6$ haloalkyl;
R2 is selected from the group consisting of hydrogen, $C_1$-$C_4$ alkyl and $C_1$-$C_4$ alkoxy;
R3, R7 and R8 are each independently selected from the group consisting of hydrogen, halogen, cyano, $C_1$-$C_4$ alkyl, and $C_1$-$C_4$ alkoxy;
R4 and R5 are each independently selected from the group consisting of hydrogen and $C_1$-$C_4$ alkyl;
R6 is hydrogen;
L is selected from the group consisting of a bond, a linear —$C_1$-$C_4$-alkyl chain, a linear —$C_2$-$C_4$-alkenyl chain, and a linear —$C_2$-$C_4$-alkynyl chain;
A is a 3-10 membered heterocyclyl or aryl, each optionally substituted with one to three Ry; and
Ry is selected from the group consisting of cyano, halogen, $C_1$-$C_4$ alkyl and $C_1$-$C_4$ haloalkyl.

In a further embodiment of formula (I):
R1 is selected from the group consisting of $C_1$-$C_6$ alkyl, $C_3$-$C_5$-cycloalkyl-$C_1$-$C_6$ alkyl and $C_1$-$C_6$ haloalkyl;
R2, R3, R6, R7 and R8 are hydrogen;
R4 and R5 are each independently selected from the group consisting of hydrogen and $C_1$-$C_4$ alkyl;
L is selected from the group consisting of a bond, a linear —$C_1$-$C_4$-alkyl chain, a linear —$C_2$-$C_4$-alkenyl chain, and a linear —$C_2$-$C_4$-alkynyl chain;
A is a 3-10 membered heterocyclyl or aryl, each optionally substituted with one to three Ry; and
Ry is selected from the group consisting of cyano, halogen, $C_1$-$C_4$ alkyl, and $C_1$-$C_4$ haloalkyl.

In one embodiment of the present invention there is provided a compound of formula (II)

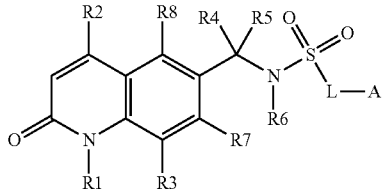

(II)

wherein the substituents are as defined above; or salts or N-oxides thereof. Preferred values of R1, R2, R3, R4, R5, R6, R7, R8, L, A, Rx, Ry and Rz for compounds of formula (II) are, in any combination, as set out above.

In a further embodiment of the present invention there is provided a compound of formula (III)

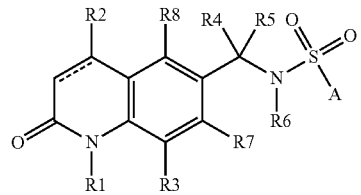

(III)

wherein the substituents are as defined above; or salts or N-oxides thereof. Preferred values of R1, R2, R3, R4, R5, R6, R7, R8, L, A, Rx, Ry and Rz for compounds of formula (III) are, in any combination, as set out above.

In another embodiment of the present invention there is provided a compound of formula (IV)

(IV)

wherein:
R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$ alkenyl, $C_3$-$C_7$ alkynyl, aryl-$C_1$-$C_7$ alkyl, (3-6 membered heterocyclyl)-$C_1$-$C_7$ alkyl, phenyl, $C_3$-$C_5$ cycloalkyl and a 4-6 membered heterocyclyl, each optionally substituted with one to three Rx;
R2 is selected from the group consisting of hydrogen, cyano, $C_1$-$C_4$ alkyl, $C_1$-$C_4$ alkoxy, $C_1$-$C_4$ haloalkyl, $C_1$-$C_4$ haloalkoxy and $C_3$-$C_4$ cycloalkyl;
R3, R7 and R8 are independently selected from the group consisting of hydrogen, halogen, cyano, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy and $C_3$-$C_4$ cycloalkyl;
R4 and R5 are independently selected from the group consisting of hydrogen, $C_1$-$C_4$ alkyl, $C_1$-$C_4$ haloalkyl and $C_3$-$C_4$ cycloalkyl;
or R4 and R5 can form, together with the atom or atoms they are directly attached to, a $C_3$-$C_4$ cycloalkyl or $C_3$-$C_4$ heterocyclyl;
R6 is selected from the group consisting of hydrogen, $C_1$-$C_4$ alkyl, $C_3$-$C_4$ alkenyl, $C_3$-$C_4$ alkynyl, and $C_1$-$C_3$ alkoxy-$C_1$-$C_4$-alkyl;
A is hydrogen, $C_1$-$C_7$ alkyl, $C_3$-$C_5$ cycloalkyl, 3-10 membered heterocyclyl or aryl, each optionally substituted with one to three Ry;
Rx is, independently of each other, selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl;
Ry is, independently of each other, selected from the group consisting of halogen, cyano, $C_1$-$C_4$ alkyl, $C_1$-$C_4$ alkoxy, $C_1$-$C_4$ haloalkyl, $C_1$-$C_4$ haloalkyloxy, $C_1$-$C_4$ alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl which cycloalkyl is unsubstituted or substituted by one or more Rz; and Rz is independently selected from the group consisting of halogen, $C_1$-$C_4$-alkyl and $C_1$-$C_4$-haloalkyl;

wherein A is not butyl when either R4 or R5 is methyl;

and wherein R1 is not methyl when R2, R3, R4, R5, R6, R7 and R8 are each hydrogen;

or salts or N-oxides thereof.

Preferred values of R1, R2, R3, R4, R5, R6, R7, R8, A, Rx, Ry and Rz for compounds of formula (IV) are, in any combination, as set out above.

Table 1 below includes examples of compounds of the present invention.

TABLE 1

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

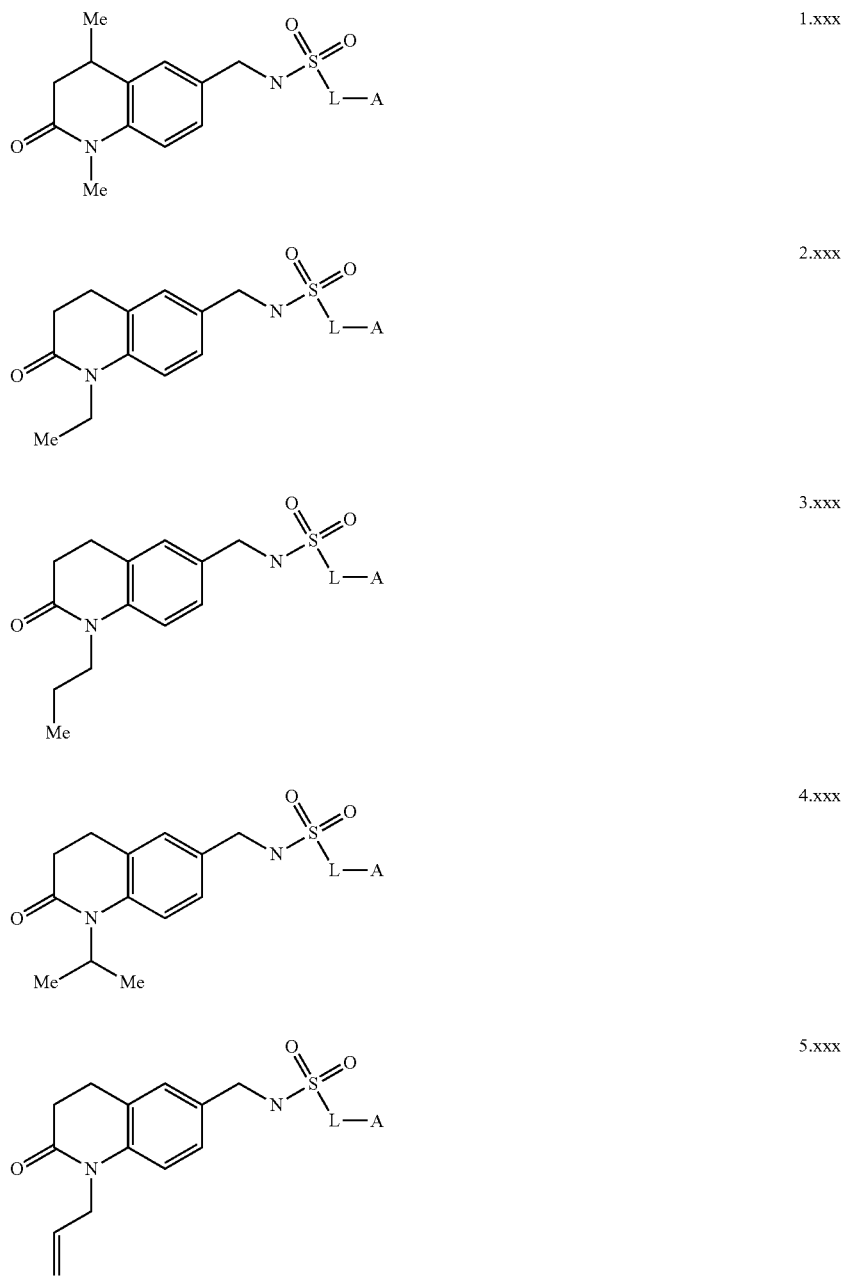

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

6.xxx 7.xxx 8.xxx 9.xxx 10.xxx 11.xxx

TABLE 1-continued
Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.
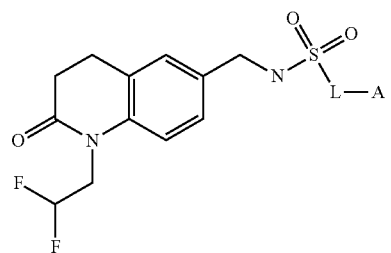
12.xxx
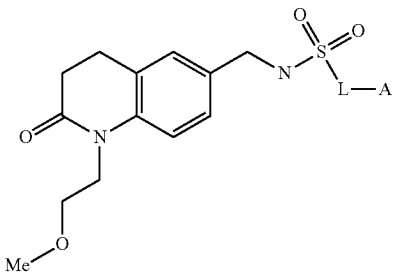
13.xxx
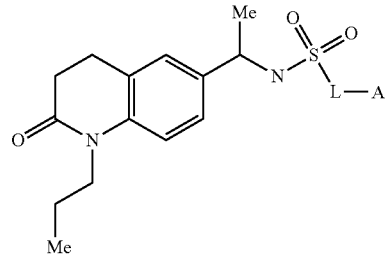
14.xxx
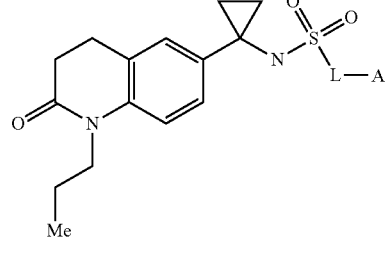
15.xxx
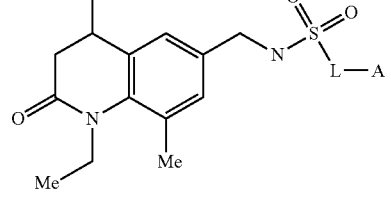
16.xxx
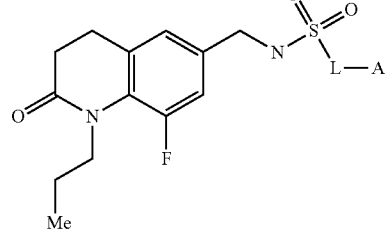
17.xxx TABLE 1-continued
Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.
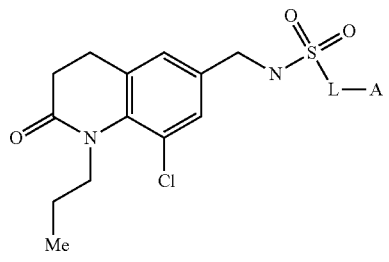
18.xxx
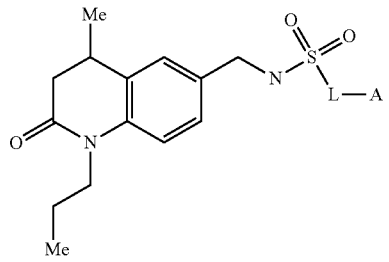
19.xxx
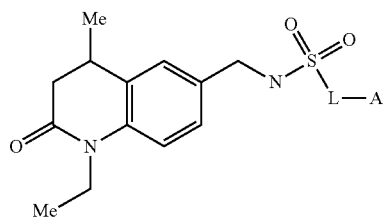
20.xxx
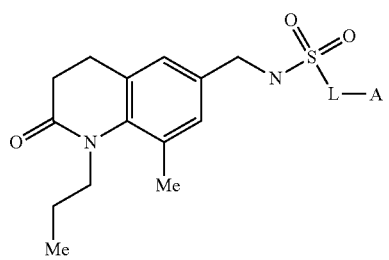
21.xxx
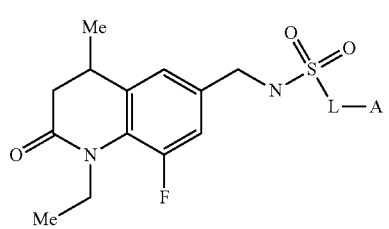
22.xxx
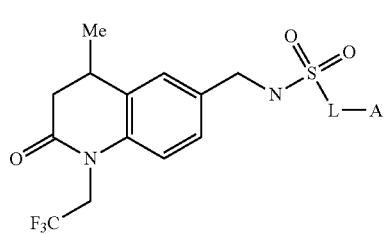
23.xxx TABLE 1-continued Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

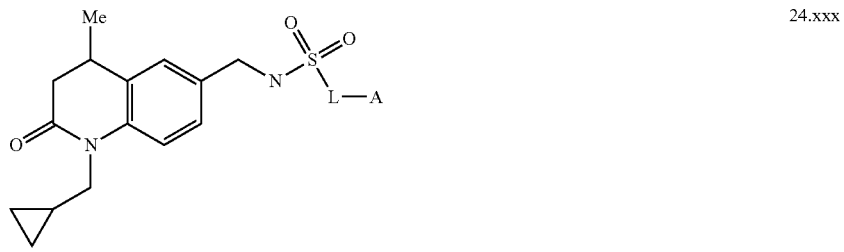

24.xxx

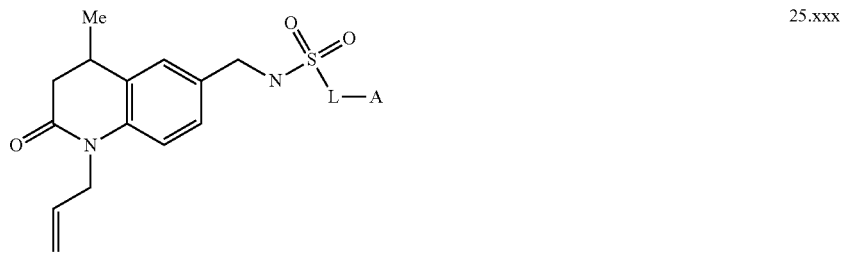

25.xxx

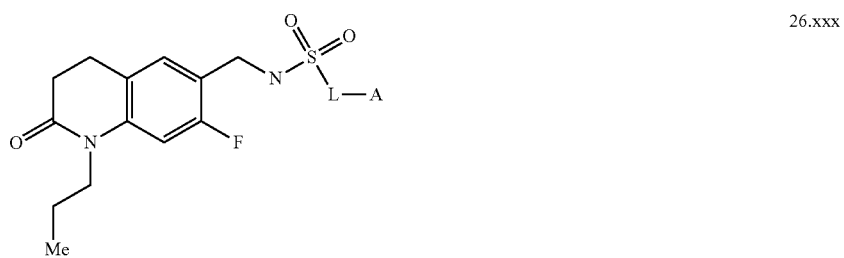

26.xxx

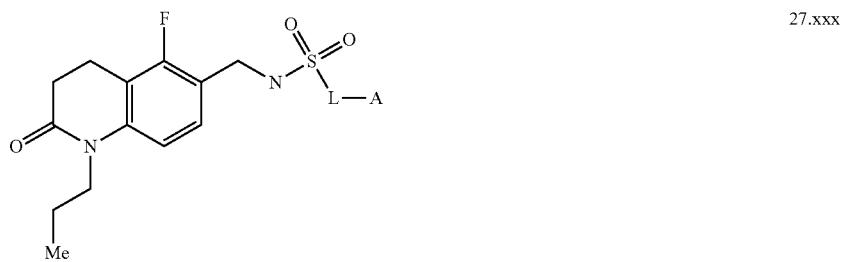

27.xxx

| Compound | L | A |
|---|---|---|
| x.001 | bond | phenyl |
| x.002 | bond | 4-bromophenyl |
| x.003 | bond | 3-chlorophenyl |
| x.004 | bond | 4-chlorophenyl |
| x.005 | bond | 2,6-difluorophenyl |
| x.006 | bond | 2,4-difluorophenyl |
| x.007 | bond | 2-fluorophenyl |
| x.008 | bond | 3-fluorophenyl |
| x.009 | bond | 4-fluorophenyl |
| x.010 | bond | 4-methoxyphenyl |
| x.011 | bond | o-tolyl |
| x.012 | bond | p-tolyl |
| x.013 | bond | p-tolylmethyl |
| x.014 | bond | 2,4-dimethylphenyl |
| x.015 | bond | 4-(trifluoromethyl)phenyl |
| x.016 | bond | 4-isopropoxyphenyl |
| x.017 | bond | 2-bromophenyl |
| x.018 | bond | cyclopropyl |
| x.019 | bond | butyl |
| x.020 | bond | 4,4,4-trifluorobutyl |
| x.021 | —CH$_2$— | phenyl |
| x.022 | —CH$_2$— | 4-bromophenyl |
| x.023 | —CH$_2$— | 2-fluorophenyl |

TABLE 1-continued

Each of the following structures may be combined with the substituent combinations listed in the table below, such that specific compound 1.001 is structure 1.xxx combined with compound x.001, specific compound 5.123 is structure 5.xxx combined with compound x.123 in the table, and so on.

| | | |
|---|---|---|
| x.024 | —$CH_2$— | p-tolyl |
| x.025 | —$CH_2$— | 2,4-difluorophenyl |
| x.026 | —$CH_2$— | 2,6-difluorophenyl |
| x.027 | —$CH_2$— | 4-(cyclopropyl)phenyl |
| x.028 | —$CH_2$— | 4-nitrophenyl |
| x.029 | —$CH_2$— | 2,4-dichlorophenyl |
| x.030 | —$CH_2$— | 3-fluorophenyl |
| x.031 | —$CH_2$— | 4-chlorophenyl |
| x.032 | —$CH_2$— | 6-(trifluoromethyl)-3-pyridyl |
| x.033 | —$CH_2$— | 3-(trifluoromethyl)phenyl |
| x.034 | —$CH_2$— | —$CH_2$—methoxycarbonyl |
| x.035 | —$CH_2$—$CH_2$— | phenyl |
| x.036 | —$CH_2$— | 4-bromo-2-fluoro-phenyl |
| x.037 | —$CH_2$— | 2,5-difluorophenyl |
| x.038 | —$CH_2$— | 2,3-difluorophenyl |
| x.039 | —$CH_2$— | 2-bromo-4-fluoro-phenyl |
| x.040 | —$CH_2$— | 2-bromo-4-chloro-phenyl |
| x.041 | —$CH_2$— | 2-cyanophenyl |
| x.042 | —$CH_2$— | 4-cyano-2-fluoro-phenyl |
| x.043 | —$CH_2$— | 2-cyanophenyl |
| x.044 | —$CH_2$— | 2-chloro-4-fluoro-phenyl |
| x.045 | —$CH_2$— | 4-tert-butylphenyl |
| x.046 | —$CH_2$— | 4-(trifluoromethoxy)phenyl |
| x.047 | —$CH_2$— | 4-(trifluoromethyl)phenyl |
| x.048 | —$CH_2$— | 2-bromophenyl |
| x.049 | —$CH_2$— | 3-bromophenyl |
| x.050 | —$CH_2$— | 4-(trifluoromethylsulfanylphenyl |
| x.051 | —CH=CH— | phenyl |
| x.052 | —CH=CH— | 4-bromophenyl |
| x.053 | —CH=CH— | 4-chlorophenyl |
| x.054 | —CH=CH— | 5-chlorothiazol-2-yl |
| x.055 | —CH=CH— | 5-chloro-2-thienyl |
| x.056 | —CH=CH— | 2-fluorophenyl |
| x.057 | —CH=CH— | 4-fluorophenyl |
| x.058 | —CH=CH— | 5-methyl-2-thienyl |
| x.059 | —CH=CH— | p-tolyl |
| x.060 | —CH=CH— | methyl |
| x.061 | bond | (5-methyl-2-thienyl) |
| x.062 | bond | propyl |
| x.063 | bond | (1-methylimidazol-4-yl) |
| x.064 | bond | (2,5-dichloro-3-thienyl) |
| x.066 | —$CH_2$—CH=CH— | methyl |
| x.067 | bond | 3,3,3-trifluoropropyl |
| x.068 | bond | 3-thienyl |
| x.069 | —CH=CH— | 3-chlorophenyl |
| x.070 | —CH=CH— | 3-bromophenyl |
| x.071 | —$CH_2$—CH=CH— | H |
| x.072 | bond | 2-thienyl |
| x.073 | bond | (5-chloro-2-thienyl) |
| x.074 | bond | 1-napthyl |
| x.075 | bond | 2-napthyl |
| x.076 | bond | 4-ethylphenyl |
| x.077 | bond | 4-propylphenyl |
| x.078 | bond | 4-cyclopropylphenyl |
| x.079 | bond | 2-fluoro-4-methylphenyl |

In one embodiment, the compounds of the present invention are applied in combination with an agriculturally acceptable adjuvant. In particular, there is provided a composition comprising a compound of the present invention and an agriculturally acceptable adjuvant. There may also be mentioned an agrochemical composition comprising a compound of the present invention.

The present invention provides a method of improving the tolerance of a plant to abiotic stress, wherein the method comprises applying to the plant, plant part, plant propagation material, or plant growing locus a compound, composition or mixture according to the present invention.

The present invention provides a method for regulating or improving the growth of a plant, wherein the method comprises applying to the plant, plant part, plant propagation material, or plant growing locus a compound, composition or mixture according to the present invention. In one embodiment, plant growth is regulated or improved when the plant is subject to abiotic stress conditions.

The present invention also provides a method for inhibiting seed germination of a plant, comprising applying to the seed, or a locus containing seeds, a compound, composition or mixture according to the present invention.

The present invention also provides a method for safening a plant against phytotoxic effects of chemicals, comprising applying to the plant, plant part, plant propagation material, or plant growing locus a compound, composition or mixture according to the present invention.

Suitably the compound or composition is applied in an amount sufficient to elicit the desired response.

According to the present invention, "regulating or improving the growth of a crop" means an improvement in plant vigour, an improvement in plant quality, improved tolerance to stress factors, and/or improved input use efficiency.

An 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

An 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

An 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to biotic and/or abiotic stress factors, and in particular abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients. In particular, the compounds or compositions of the present invention are useful to improve tolerance to drought stress.

An 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other effects of regulating or improving the growth of a crop include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compounds of the present invention can be used alone, but are generally formulated into compositions using formulation adjuvants, such as carriers, solvents and surface-active agents (SFAs). Thus, the present invention further provides a composition comprising a compound of the present invention and an agriculturally acceptable formulation adjuvant. There is also provided a composition consisting essentially of a compound of the present invention and an agriculturally acceptable formulation adjuvant. There is also provided a composition consisting of a compound of the present invention and an agriculturally acceptable formulation adjuvant.

The present invention further provides a plant growth regulator composition comprising a compound of the present invention and an agriculturally acceptable formulation adjuvant. There is also provided a plant growth regulator composition consisting essentially of a compound of the present invention and an agriculturally acceptable formulation adjuvant. There is also provided a plant growth regulator composition consisting of a compound of the present invention and an agriculturally acceptable formulation adjuvant.

The present invention further provides a plant abiotic stress management composition comprising a compound of the present invention and an agriculturally acceptable formulation adjuvant. There is also provided a plant abiotic stress management composition consisting essentially of a compound of the present invention and an agriculturally acceptable formulation adjuvant. There is also provided a plant abiotic stress management composition consisting of a compound of the present invention and an agriculturally acceptable formulation adjuvant.

The present invention further provides a seed germination inhibitor composition comprising a compound of the present invention and an agriculturally acceptable formulation adjuvant. There is also provided a seed germination inhibitor composition consisting essentially of a compound of the present invention and an agriculturally acceptable formulation adjuvant. There is also provided a seed germination inhibitor composition consisting of a compound of the present invention and an agriculturally acceptable formulation adjuvant.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of the present invention and from 1 to 99.9% by weight of a formulation adjuvant which preferably includes from 0 to 25% by weight of a surface-active substance. The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultralow volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of the present invention.

Dustable powders (DP) may be prepared by mixing a compound of the present invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of the present invention with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the present invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the present invention and one or more powdered solid diluents or carriers, or from preformed blank granules by absorbing a compound of the present invention (or a solution thereof, in a suitable agent) in a porous granular material (such as pumice, attapulgite clays, fuller's earth, kieselguhr, diatomaceous earths or ground corn cobs) or by adsorbing a compound of the present invention (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the present invention in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of the present invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the present invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the present invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the present invention. SCs may be prepared by ball or bead milling the solid compound of the present invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the present invention may be dry milled and added to water, containing agents hereinbefore described, to produce the desired end product.

Aerosol formulations comprise a compound of the present invention and a suitable propellant (for example n-butane). A compound of the present invention may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of the present invention and, optionally, a carrier or diluent therefor. The polymeric shell may be produced by either an interfacial polycondensation reaction or by a coacervation procedure. The compositions may provide for controlled release of the compound of the present invention and they may be used for seed treatment. A compound of the present invention may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of the present invention. Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of the present invention). Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compound or composition of the present invention may be applied to a plant, part of the plant, plant organ, plant propagation material or a plant growing locus.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound or composition of the present invention may be applied pre-emergence or post-emergence. Suitably, where the composition is used to regulate the growth of crop plants or enhance the tolerance to abiotic stress, it may be applied post-emergence of the crop. Where the composition is used to inhibit or delay the germination of seeds, it may be applied pre-emergence.

The present invention envisages application of the compounds or compositions of the invention to plant propagation material prior to, during, or after planting, or any combination of these.

Although active ingredients can be applied to plant propagation material in any physiological state, a common approach is to use seeds in a sufficiently durable state to incur no damage during the treatment process. Typically, seed would have been harvested from the field; removed from the plant; and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

The rates of application of compounds of the present invention may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of the present invention according to the invention are generally applied at a rate of from 1 to 2000 g/ha, especially from 5 to 1000 g/ha. For seed treatment the rate of application is generally between 0.0005 and 150 g per 100 kg of seed.

The compounds and compositions of the present invention may be applied to dicotyledonous or monocotyledonous crops. Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®. Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compounds of the present invention may also be used to inhibit or delay the germination of seeds of non-crop plants, for example as part of an integrated weed control program. A delay in germination of weed seeds may provide a crop seedling with a stronger start by reducing competition with weeds. Alternatively compounds of the present invention may be used to delay the germination of seeds of crop plants, for example to increase the flexibility of timing of planting for the grower.

Normally, in the management of a crop a grower would use one or more other agronomic chemicals or biologicals in addition to the compound or composition of the present invention. There is also provided a mixture comprising a compound or composition of the present invention, and a further active ingredient.

Examples of agronomic chemicals or biologicals include pesticides, such as acaricides, bactericides, fungicides, herbicides, insecticides, nematicides, plant growth regulators, crop enhancing agents, safeners as well as plant nutrients and plant fertilizers. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops. The combination may also encompass specific plant traits incorporated into the plant using any means, for example conventional breeding or genetic modification.

The present invention also provides the use of a compound of formula (I), formula (II), formula (III), or formula (IV), or a composition comprising a compound according to formula (I), (II), (III), or (IV) and an agriculturally acceptable formulation adjuvant, for improving the tolerance of a plant to abiotic stress, regulating or improving the growth of a plant, inhibiting seed germination and/or safening a plant against phytotoxic effects of chemicals.

There is also provided the use of a compound, composition or mixture of the present invention, for improving the tolerance of a plant to abiotic stress, regulating or improving the growth of a plant, inhibiting seed germination and/or safening a plant against phytotoxic effects of chemicals.

The compounds of the invention may be made by the following methods.

PREPARATION EXAMPLES

Schemes 1-7 provide methods of preparing the compounds of formula (I), compounds of formula (II) and compounds of formula (III) of the present invention, wherein R4, R5, R6, R7 and R8 are H when present.

SCHEME 1:

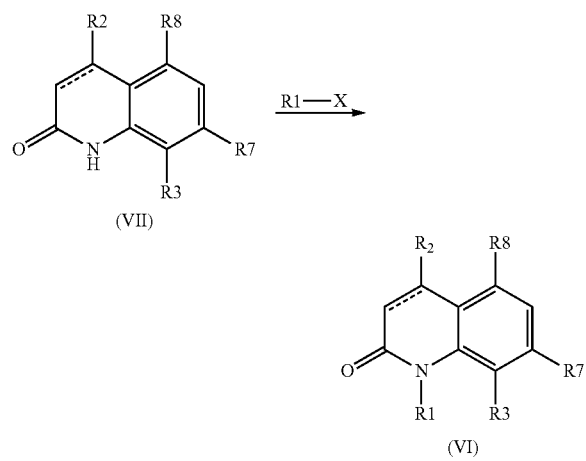

(VII)

(VI)

Compounds of formula (VII) are commercially available or can be made by methods known to a person skilled in the art. Compounds of formula (VI) may be prepared from a compound of formula (VII) by reaction with an alkylating agent of formula R1-X, wherein X is a leaving group such as halogen, mesylate, triflate or tosylate. For example, R1-X can be propyl iodide, ethyl iodide, allyl bromide or methyl iodide. Such reactions are usually carried out in the presence of a base, and optionally in the presence of a nucleophilic catalyst.

SCHEME 2:

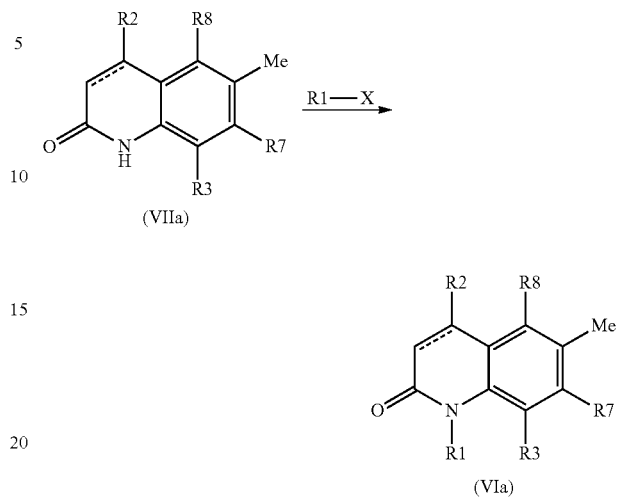

(VIIa)

(VIa)

Compounds of formula (VIIa) are commercially available or can be made by methods known to a person skilled in the art. Compounds of formula (VIa) may be prepared from a compound of formula (VIIa) by reaction with an alkylating agent of formula R1-X, wherein X is a leaving group such as halogen, mesylate, triflate or tosylate. For example, R1-X can be propyl iodide, ethyl iodide, allyl bromide or methyl iodide. Such reactions are usually carried out in the presence of a base, and optionally in the presence of a nucleophilic catalyst.

SCHEME 3:

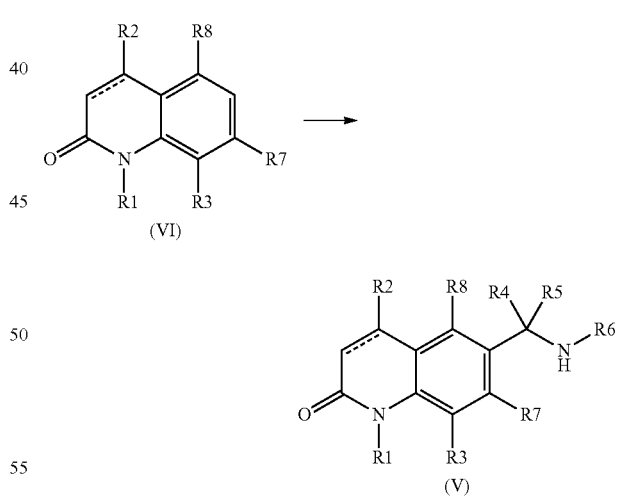

(VI)

(V)

Compounds of formula (V), wherein R4, R5 and R6 are H, may be prepared from a compound of formula (VI) by reaction with 2-chloro-N-(hydroxymethyl)acetamide in a solvent such as acetic acid, and optionally in the presence of stronger acid such as sulfuric acid, followed by hydrolysis of the resulting 2-chloroacetamide with an acid such as HCl in an alcoholic solvent. Compound (V) can be obtained as its hydrochloride salt or a free amine after neutralization with a base.

SCHEME 4:

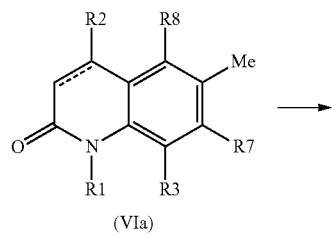

Compounds of formula (V), wherein R4 and R5 are H, may be prepared from a compound of formula (VIb) wherein X is a leaving group such as halogen, by reaction with an amine of formula R6NH$_2$ or its hydrochloride salt of formula R6NH$_3$Cl, in the presence or not of a base such as triethyl amine or diisopropylamine. For example, R6NH$_2$ can be ammonia, methyl amine or ethyl amine.

The compound of formula (VIb) may be obtained from a compound of formula (VIa) wherein X is a leaving group such as Cl or Br, by radical reaction with N-bromosuccinimide or N-chlorosuccinimide in the presence of an initiator such as AIBN or dibenzoyl peroxide.

SCHEME 5:

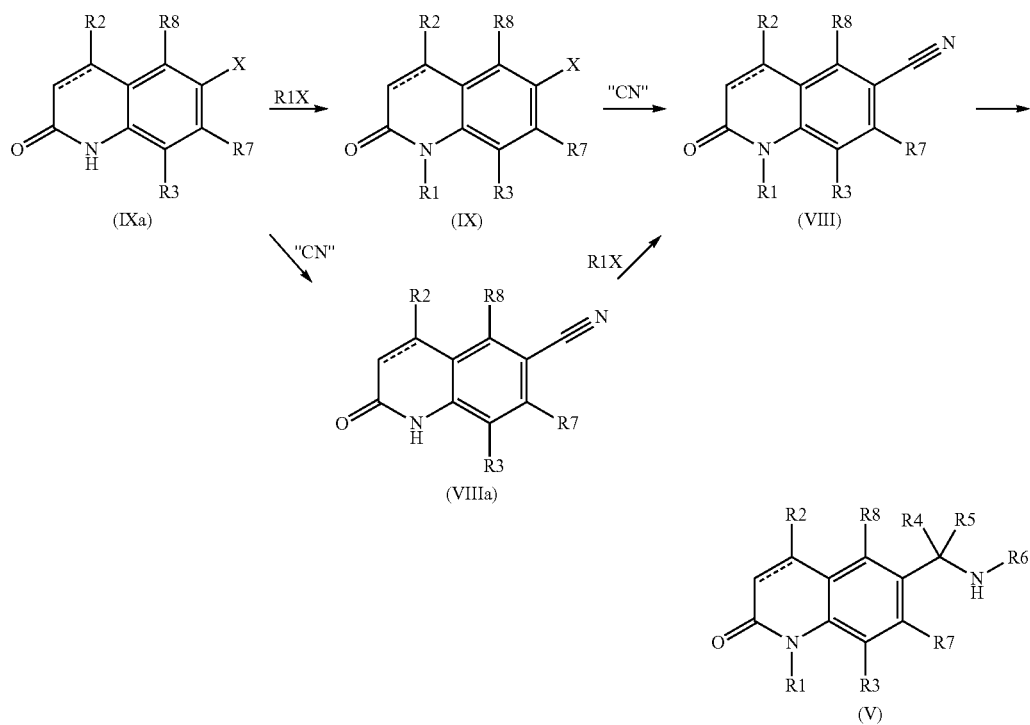

Compounds of formula (V), wherein R4, R5 and R6 are H, may be prepared from a compound of formula (VIII) by reduction of the cyano moiety under hydrogen atmosphere in the presence of a catalyst such as palladium on charcoal, or by reducing agent such as sodium borohydride in the presence of a catalyst such as nickel chloride or cobalt chloride for example.

The compound of formula (VIII) may be obtained from a compound of formula (IX) wherein X is a leaving group such as Cl or Br, I or OTf by a coupling reaction with a cyanide salt such as CuCN, NaCN, K$_3$[Fe(CN)$_6$], in the presence or not of a catalyst such as palladium (0) or cupper, eventually with an additional ligant as described in the literature (see Zanon et al, *J. Am. Chem Soc.* 2003, 125, 2890-2891, Buchwald, S & all, *Angew. Chem. Int. Ed.* 2013, 52: 10035-10039).

The compound of formula (IX) may be obtained from a compound of formula (IXa) by reaction with an alkylating agent of formula R1-X, wherein X is a leaving group such as halogen, mesylate, triflate or tosylate. For example, R1-X can be propyl iodide, ethyl iodide, allyl bromide, or methyl iodide. Such reactions are usually carried out in the presence of a base, and optionally in the presence of a nucleophilic catalyst.

Alternatively, compound of formula (VIII) may be obtained from a compound of formula (VIIIa) by reaction with an alkylating agent of formula R1-X, wherein X is a leaving group such as halogen, mesylate, triflate or tosylate. For example, R1-X can be propyl iodide, ethyl iodide, allyl bromide, or methyl iodide. Such reactions are usually carried out in the presence of a base, and optionally in the presence of a nucleophilic catalyst.

Compound of formula (VIIIa) may be prepared from compound (IXa) wherein X is a leaving group such as Cl or Br, I or OTf by a coupling reaction with a cyanide salt as described for compound (VIIIa)

SCHEME 6:

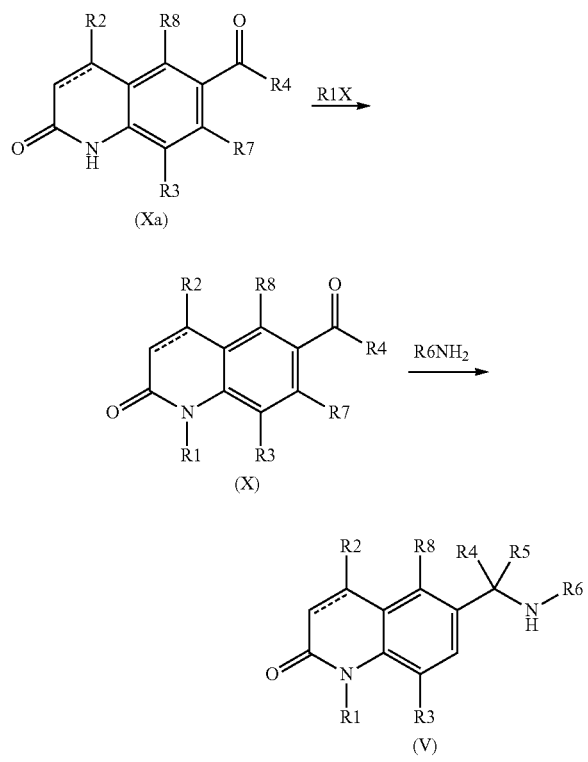

Compounds of formula (V) wherein R5 is H, may be prepared from a compound of formula (X) by amino reduction of the carbonyl moiety in the presence of an amine of formula R6NH$_2$ or its corresponding salt in the presence of a reducing agent such as sodium cyanoborohydride and eventually of an additional organic acid such as acetic acid.

The compound of formula (X) may be obtained from a compound of formula (Xa) by reaction with an alkylating agent of formula R1-X, wherein X is a leaving group such as halogen, mesylate, triflate or tosylate. For example, R1-X can be propyl iodide, ethyl iodide, allyl bromide, or methyl iodide. Such reactions are usually carried out in the presence of a base, and optionally in the presence of a nucleophilic catalyst.

SCHEME 7:

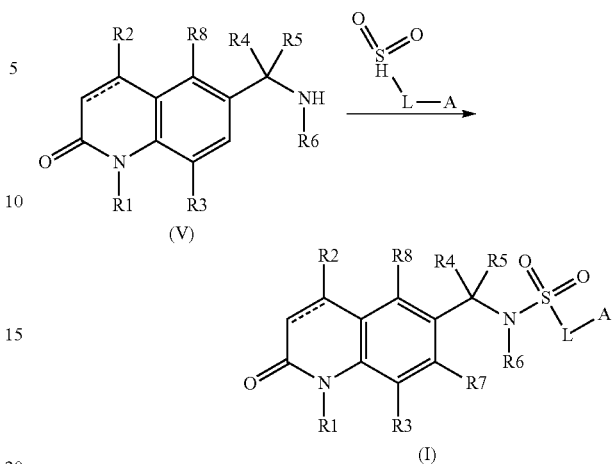

Compounds of formula (I) may be prepared from a compound of formula (V) by reaction with sulfonyl chloride of formula A-L-SO$_2$Cl. Such reactions are usually carried out in the presence of an organic base, such as N-ethyldiisopropylamine. For example, A-L-SO$_2$Cl can be benzenesulfonyl chloride, benzylsulfonyl chloride or butylsulfonyl chloride. Compounds of formula A-L-SO$_2$Cl are commercially available or can be made by methods known to a person skilled in the art.

Example P1: Preparation of 2,4-dimethyl-N-[(2-oxo-1-propyl-3,4-dihydroquinolin-6-yl)methyl]benzenesulfonamide (Compound 3.014)

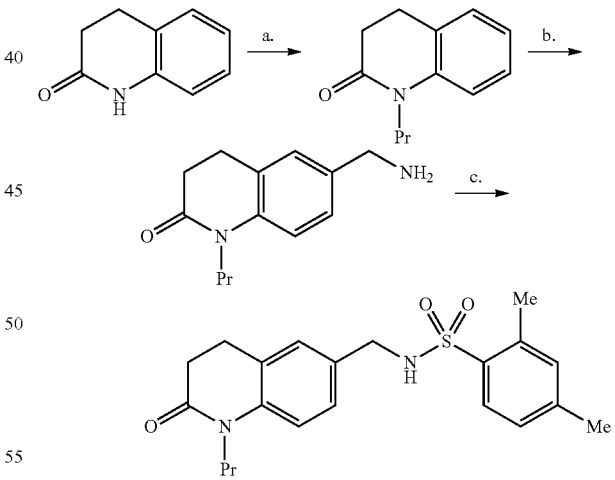

a. 1-propyl-3,4-dihydroquinolin-2-one 3,4-Dihydro-1H-quinolin-2-one (5.00 g, 34 mmol) was dissolved in dimethylformamide (DMF) (49 mL). Potassium carbonate (14.2 g, 102 mmol) was added. At room temperature, 1-bromopropane (12.5 g, 102 mmol, 9.27 mL) was added dropwise. The reaction mixture was stirred four days at room temperature and then heated for 4 h at 60° C. The reaction mixture was cooled to room temperature and poured into 200 mL of ice-water. The water-phase was extracted with 100 ml ethyl acetate (EtOAc). The combined organic phases were washed with water and brine. The organic phase was dried with $Na_2SO_4$, filtrated and concentrated to give 7.3 g of pale yellow oil. The crude product was purified on silica gel to give 1-propyl-3,4-dihydroquinolin-2-one (5.2 g, 27.5 mmol, 81%) as a colorless oil. $^1$H NMR (CDCl$_3$, 400 MHz) δ 0.96 (3H, t); 1.68 (2H, sxt); 2.64 (2H, m); 2.88 (2H, m); 3.90 (2H, t); 6.99 (2H, m); 7.16 (1H, m); 7.24 (1H, m).

b. 6-(aminomethyl)-1-propyl-3,4-dihydroquinolin-2-one

1-Propyl-3,4-dihydroquinolin-2-one (4.50 g, 23.8 mmol) was added to a solution of acetic acid (234 mL) and sulfuric acid (2.4 mL). At room temperature, 2-chloro-N-(hydroxymethyl)acetamide (3.53 g, 28.5 mmol) was added. The reaction mixture was stirred for 72 h. The reaction mixture was poured into ice, and the mixture was extracted with tert-butyl methyl ether. The combined organic phases were washed with brine. The organic phase was dried with $Na_2SO_4$, filtrated and concentrated. 7.8 g of crude amide was obtained and purified on silica gel to give 4.1 g of the corresponding 2-chloroacetamide, which was further stirred in petrol ether, filtrated and dried to give 3.4 g of a white solid.

The resulting 2-chloroacetamide was dissolved into a 1:1 mixture of HCl conc./EtOH (25 mL), and then heated to reflux for 3 h, followed by stirring overnight. The reaction mixture was heated again for 2 h at reflux. The solvent was evaporated under reduced pressure and the residue was stirred in ether, filtrated and dried to give 6-(aminomethyl)-1-propyl-3,4-dihydroquinolin-2-one hydrochloride (3.26 g, 12.8 mmol, 54% yield) as a beige solid. $^1$H NMR (DMSO, 400 MHz) δ 0.87 (3H, t); 1.51 (2H, sxt); 2.53 (2H, m); 2.85 (2H, t); 3.87 (2H, t); 3.94 (2H, q); 4.86 (2H, br s); 7.18 (1H, d); 7.37 (1H, s); 7.41 (1H, d).

c. 2,4-dimethyl-N-[(2-oxo-1-propyl-3,4-dihydroquinolin-6-yl)methyl]benzenesulfonamide (Compound 3.014)

6-(aminomethyl)-1-propyl-3,4-dihydroquinolin-2-one (0.055 g, 0.216 mmol) was stirred in EtOAc (4 mL). The reaction mixture was cooled on ice. Diisopropylethylamine (0.132 mL, 0.756 mmol) was added and then 2,4-dimethylbenzenesulfonyl chloride (0.059 g, 0.281 mmol). The reaction mixture was stirred 3 h at 50° C. The reaction mixture was concentrated. The crude product was purified on silica gel to give 2,4-dimethyl-N-[(2-oxo-1-propyl-3,4-dihydroquinolin-6-yl)methyl]benzenesulfonamide (59.4 mg, 0.154 mmol, 71% yield) as a white solid. Mp.: 166°-167° C.; $^1$H NMR (CDCl$_3$, 400 MHz) δ 0.94 (3H, t); 1.62 (2H, sxt); 2.37 (3H, s); 2.58 (4H, m); 2.78 (2H, m); 3.85 (2H, t); 4.05 (2H, d, J=6.2); 4.89 (1H, t); 6.86 (1H, d); 6.95 (1H, s); 7.04 (1H, dd); 7.10 (2H, m).

Example P2: Preparation of N-[(2-oxo-1-propyl-6-quinolyl)methyl]benzenesulfonamide (Compound 7.001)

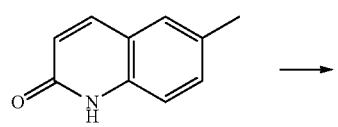

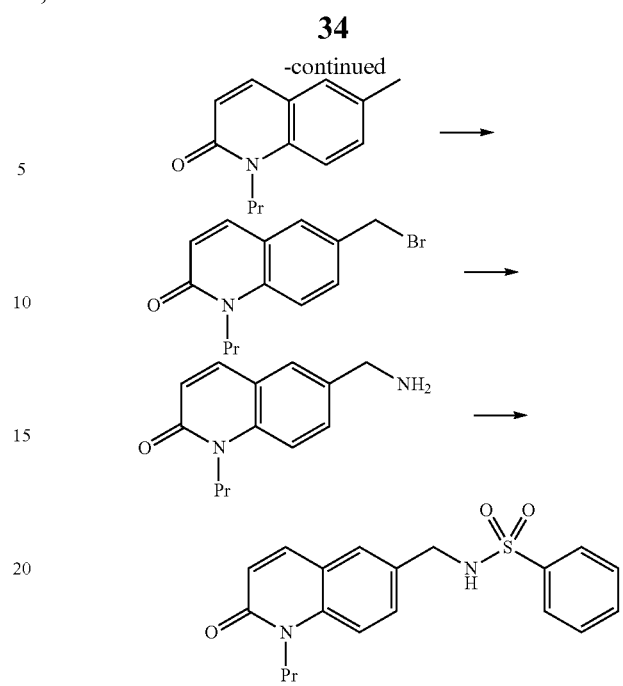

a. 6-methyl-1-propyl-quinolin-2-one

6-Methyl-1H-quinolin-2-one (5.00 g, 31.41 mmol) was dissolved in DMF (50 mL). Potassium carbonate (8.68 g, 62.8 mmol) was added, followed by 1-bromopropane (19.3 g, 157 mmol, 14.3 mL). The reaction mixture was stirred overnight at room temperature and then poured into 200 mL of ice-water. The water-phase was extracted with ethyl acetate and the combined organic phases were washed with water and brine. The organic phase was dried with $Na_2SO_4$, filtrated and concentrated to give 9.1 g of pale yellow oil. The crude product was purified on silica gel to give 6-methyl-1-propyl-quinolin-2-one (2.3 g, 11 mmol, 36%) as a colorless oil. $^1$H NMR (400 MHz, CDCl$_3$) δ ppm 1.04 (t, 3H), 1.73-1.82 (m, 2H), 2.41 (s, 3H), 4.20-4.27 (m, 2H), 6.65-6.70 (m, 1H), 7.26 (s, 1H), 7.33-7.39 (m, 2H), 7.60 (d, 1H); LC-MS (Method A): RT 0.90, (202, M+H$^+$).

b. 6-(bromomethyl)-1-propyl-quinolin-2-one

6-Methyl-1-propyl-quinolin-2-one (2.5 g, 12 mmol) was solved in a solution of carbon tetrachloride (5 mL) and 1-bromopyrrolidine-2,5-dione (2.5 g, 14 mmol). The reaction mixture was stirred and heated at 80° C. then azobisisobutyronitrile (0.2 g, 1.2 mmol) was added. The resulting was stirred at 80° C. for 6 h and cooled. Water was added and the mixture was extracted with ethyl acetate. The combined organic phases were washed with brine, dried with $Na_2SO_4$, filtrated and concentrated to give 0.61 g of brown oil. The crude product was purified on silica gel to give 6-(bromomethyl)-1-propyl-quinolin-2-one (2.6 g, 9.3 mmol, 75%). $^1$H NMR (400 MHz, CDCl$_3$) δ ppm 1.02-1.08 (m, 3H), 1.77 (sxt, 2H), 4.19-4.29 (m, 2H), 4.58 (s, 2H), 6.72 (d, 1H), 7.31-7.36 (m, 1H), 7.56-7.66 (m, 3H); LC-MS (Method A): RT 0.94, (280, M+H$^+$).

c. 6-(aminomethyl)-1-propyl-quinolin-2-one 6-(Bromomethyl)-1-propyl-quinolin-2-one (1.6 g, 5.7 mmol) was dissolved in a solution of NH$_3$/MeOH (41 mL, 7 mol/L). The yellow solution was stirred for overnight, after complete conversion the solution was concentrated on vacuum and purified on silica gel to give 6-(aminomethyl)-1-propyl-quinolin-2-one (710 mg, 3.28 mmol, 57%); $^1$H NMR (400 MHz, MeOH) δ ppm 1.03 (t, 3H), 1.72-1.81 (m, 2H), 4.20 (s, 2H), 4.29-4.35 (m, 2H), 6.72 (d, 1H), 7.66-7.74 (m, 2H), 7.78 (d, 1H), 7.92 (d, 1H); LC-MS (Method A): RT 0.26, (218, M+H+).

d. N-[(2-oxo-1-propyl-6-quinolyl)methyl]benzene-sulfonamide (Compound 7.001)

6-(Aminomethyl)-1-propyl-quinolin-2-one (0.100 g, 0.462 mmol) was stirred in EtOAc (4 mL). The reaction mixture was cooled on ice. Diisopropylethylamine (0.179 mg, 1.38 mmol) was added and then benzenesulfonyl chloride (0.089 g, 0.508 mmol). The reaction mixture was stirred 1 h and concentrated. The crude product was purified on silica gel to give N-[(2-oxo-1-propyl-6-quinolyl)methyl]benzenesulfonamide (86 mg, 52% yield) as a white solid. Mp.: 204°-206° C.; 1H NMR (400 MHz, DMSO-d6) δ ppm 0.93 (t, 3H), 1.60 (sxt, 2H), 4.06 (d, 2H), 4.11-4.21 (m, 2H), 6.53-6.64 (m, 1H), 7.51 (s, 1H), 7.41-7.48 (m, 2H), 7.51-7.64 (m, 3H), 7.76-7.86 (m, 3H), 8.21 (t, 1H); LC-MS (Method A): RT 0.85, (357, M+H+).

Example P3: Preparation of N-[1-(2-oxo-1-propyl-3,4-dihydroquinolin-6-yl)ethyl]benzenesulfonamide (Compound 14.001)

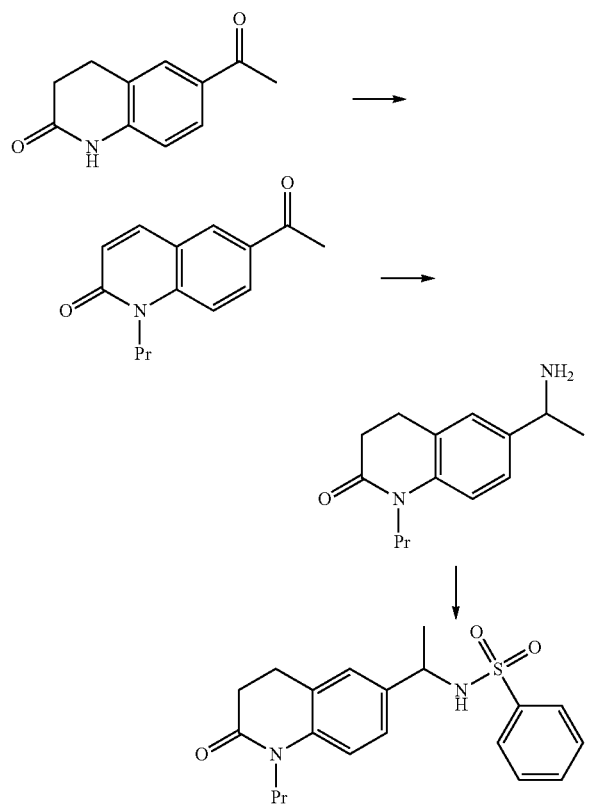

a. Preparation of 6-acetyl-1-propyl-3,4-dihydroquinolin-2-one

6-Acetyl-3,4-dihydro-1H-quinolin-2-one (500 mg, 2.64 mmol) was dissolved in DMF (5 mL) and potassium carbonate (0.547 g, 3.96 mmol) was added followed by 1-bromopropane (0.487 g, 3.96 mmol, 0.36 mL). The reaction mixture was stirred overnight at room temperature and more potassium carbonate (0.550 g, 1.5 eq.) and 1-bromopropane (0.18 mL, 0.75 eq.) were added. The reaction mixture was heated at 50° C. until to have a complete conversion, cooled to room temperature and poured into ice-water. The water-phase was extracted with ethyl acetate. The combined organic phases were washed with water and brine, dried with $Na_2SO_4$, filtrated and concentrated. The crude product was purified on silica gel to give 6-acetyl-1-propyl-3,4-dihydroquinolin-2-one (499 mg, 2.15 mmol, 81%) as a white solid. Mp.: 90-93° C.; $^1$H NMR (400 MHz, CDCl3) δ ppm 0.97 (t, 3H), 1.62-1.72 (m, 2H), 2.57-2.59 (m, 3H), 2.68 (dd, 2H), 2.93-2.98 (m, 2H), 3.89-3.97 (m, 2H), 7.03 (d, 1H), 7.77-7.88 (m, 2H); LC-MS (Method A): RT 0.84, (232, M+H+).

b. Preparation of 6-(1-aminoethyl)-1-propyl-3,4-dihydroquinolin-2-one

6-Acetyl-1-propyl-3,4-dihydroquinolin-2-one (480 mg, 2.08 mmol) was dissolved in methanol (7 mL, 2.08 mmol) then ammonium acetate (1.62 g, 20.8 mmol) and sodium cyanoborohydride (0.686 g, 10.4 mmol) were added. The reaction mixture was stirred at room temperature overnight. The solvent was removed under reduced pressure and the residue was dissolved in ethyl acetate and acidified with 2M HCl (until pH: 2). The organic layer was discarded. Then, the aqueous layer was treated with 2M NaOH (until pH: 12) and extracted 3x with ethyl acetate. The combined org layer was washed with brine, dried over $Na_2SO_4$, filtrated and evaporated to give 177 mg of uncolored oil. $^1$H NMR (400 MHz, CDCl3) δ ppm 0.96 (t, 3H), 1.38 (d, 3H), 1.66-1.72 (m, 2H), 2.63 (dd, 2H), 2.84-2.91 (m, 2H), 3.85-3.91 (m, 2H), 4.06-4.16 (m, 2H), 6.94 (d, 1H), 7.15-7.22 (m, 2H); LC-MS (Method A): RT 0.76, (234, M+H+).

c. N-[1-(2-oxo-1-propyl-3,4-dihydroquinolin-6-yl)ethyl]benzenesulfonamide (Compound 14.001)

6-(1-Aminoethyl)-1-propyl-3,4-dihydroquinolin-2-one (0.050 g, 0.215 mmol) was stirred in EtOAc (2 mL). The reaction mixture was cooled on ice. Diisopropylethylamine (0.093 mL, 0.538 mmol) was added and then benzenesulfonyl chloride (0.039 g, 0.215 mmol). The reaction mixture was stirred overnight and concentrated. The crude product was purified on silica gel to give N-[(2-oxo-1-propyl-6-quinolyl)methyl]benzenesulfonamide (49 mg, 61% yield) as a colourless gum. $^1$H NMR (400 MHz, CHLOROFORM-d) δ ppm 0.94 (t, 3H), 1.42 (d, 3H), 1.62 (sxt, 2H), 2.49-2.59 (m, 2H), 2.64-2.81 (m, 2H), 3.77-3.89 (m, 2H), 4.47 (quin, 1H), 5.08-5.26 (m, 1H), 6.79 (d, 1H), 6.84 (d, 1H), 6.99 (dd, 1H), 7.33-7.42 (m, 2H), 7.44-7.52 (m, 1H), 7.67-7.80 (m, 2H); LC-MS (Method A): RT 0.93, (373, M+H+).

Example P4: Preparation of N-[1-(2-oxo-1-propyl-3,4-dihydroquinolin-6-yl)cyclopropyl]benzenesulfonamide (Compound 15.001)

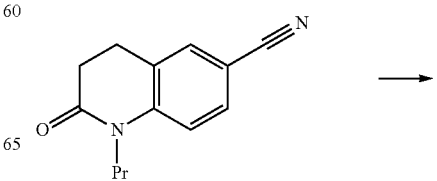

-continued

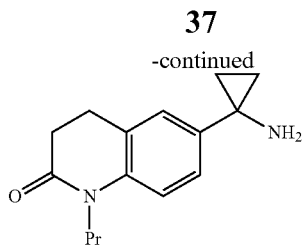

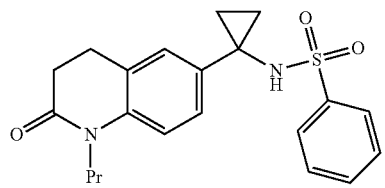

a. Preparation of 6-(1-aminocyclopropyl)-1-propyl-3,4-dihydroquinolin-2-one

Under argon, 2-oxo-1-propyl-3,4-dihydroquinoline-6-carbonitrile (0.215 g, 1 mmol) was dissolved in diethyl ether (10 ml). Titanium(IV) isopropoxide (0.323 g, 1.1 mmol) was added and reaction mixture was cooled to 0° C. Ethylmagnesium bromide (1.0 mol/L) in TBME (2.2 mL, 1.9 g, 2.2 mmol) was added dropwise and stirred for 10 min then warmed up to room temperature. Bortrifluoriddiethyletherat (0.265 ml, 0.323 g) was added and stirred. A solution of hydrochloride acid (1M) was added, then TBME at the reaction mixture, aqueous layer was collected and treated with sodium hydroxide (2M) until pH=10). Then it was extracted with TBME three times. Organic layer were combined, washed with brine, dried on $Na_2SO_4$ and concentrated on vacuum. The residue was purified with silica gel to give 6-(1-aminocyclopropyl)-1-propyl-3,4-dihydroquinolin-2-one (77 mg, 0.315 mmol) as a colourless oil. $^1H$ NMR (400 MHz, $CDCl_3$) δ ppm 0.94 (d, 3H) 1.66 (sxt, 2H) 2.61-2.66 (m, 2H) 2.85-2.90 (m, 2H) 3.85-3.91 (m, 2H) 6.92 (d, 1H) 7.09-7.19 (m, 2H). LC-MS (Method A): RT 0.55, (245, M+H$^+$).

b. N-[1-(2-oxo-1-propyl-3,4-dihydroquinolin-6-yl)cyclopropyl]benzenesulfonamide (Compound 15.001)

6-(1-Aminocyclopropyl)-1-propyl-3,4-dihydroquinolin-2-one (0.050 g, 0.204 mmol) was stirred in EtOAc (2 mL). The reaction mixture was cooled on ice. Diisopropylethylamine (0.087 mL, 0.511 mmol) was added and then benzenesulfonyl chloride (0.037 g, 0.204 mmol). The reaction mixture was stirred overnight and concentrated. The crude product was purified on silica gel to give N-[1-(2-oxo-1-propyl-3,4-dihydroquinolin-6-yl)cyclopropyl]benzenesulfonamide (57 mg, 72% yield) as a colourless gum. $^1H$ NMR (400 MHz, CHLOROFORM-d) δ ppm 0.87-0.98 (m, 3H), 1.02-1.08 (m, 2H), 1.29-1.37 (m, 2H), 1.59 (sxt, 2H), 2.48-2.57 (m, 2H), 2.61-2.70 (m, 2H), 3.76-3.88 (m, 2H), 6.11 (s, 1H), 6.64-6.74 (m, 1H), 6.84 (d, 1H), 7.01 (dd, 1H), 7.24-7.32 (m, 2H), 7.36-7.44 (m, 1H), 7.61-7.68 (m, 2H); LC-MS (Method A): RT 0.93, (385, M+H$^+$).

Example P5: Preparation of 6-(aminomethyl)-1-(2,2,2-trifluoroethyl)-3,4-dihydroquinolin-2-one (Compound 11.001)

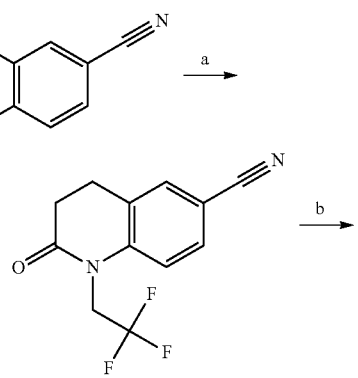

a. 2-oxo-1-(2,2,2-trifluoroethyl)-3,4-dihydroquinoline-6-carbonitrile

2-Oxo-3,4-dihydroquinoline-6-carbonitrile (0.500 g, 2.90 mmol) was dissolved in DMF (15 mL) and potassium carbonate (1.01 g, 7.26 mmol) was added followed by 2,2,2-trifluoroethyl trifluoromethanesulfonate (0.604 mL, 4.07 mmol) dropwise. The reaction mixture was heated to 50° C. and stirred for 2 h. An other 0.5 equivalent of 2,2,2-trifluoroethyl trifluoromethanesulfonate (0.216 mL) was added and the reaction mixture was stirred for another 2 h. The reaction mixture was poured on water and it was extracted with ethyl acetate. The combined organic layers were washed with water and with brine, dried over $Na_2SO_4$ and concentrated. The crude product was purified on silica gel to give 2-oxo-1-(2,2,2-trifluoroethyl)-3,4-dihydroquinoline-6-carbonitrile (0.485 g, 66%) as a pale yellow gum; $^1H$ NMR (400 MHz, CHLOROFORM-d) δ ppm 2.73-2.81 (m, 2H), 2.98-3.07 (m, 2H), 4.67 (q, 2H), 7.15 (d, 1H), 7.45-7.53 (m, 1H), 7.59 (dd, 1H); LC-MS (Method A): RT 0.84, (255, M+H$^+$).

b. 6-(aminomethyl)-1-(2,2,2-trifluoroethyl)-3,4-dihydroquinolin-2-one

2-Oxo-1-(2,2,2-trifluoroethyl)-3,4-dihydroquinoline-6-carbonitrile (0.485 g, 1.91 mmol) and Pd/C 10% (0.049 g, 0.046 mmol) were put in a flask under argon and degassed ethanol (19 mL) was added. Aqueous hydrochloric acid (32 mass %, 1.404 mL) was added and the reaction mixture was stirred under an atmosphere of molecular hydrogen overnight. The reaction mixture was filtered trough a pad of celite and concentrated to give the crude 6-(aminomethyl)-1-(2,2,2-trifluoroethyl)-3,4-dihydroquinolin-2-one (602 mg, quant) as its hydrochloride salt. The compound was used as such for the next step. $^1$H NMR (400 MHz, METHANOL-d4) δ ppm 2.70 (t, 2H), 2.98 (t, 2H), 4.08 (s, 2H), 4.74-4.85 (m, 2H), 7.26-7.47 (m, 3H); LC-MS (Method A): RT 0.30, (255, M+H$^+$).

c. N-[[2-oxo-1-(2,2,2-trifluoroethyl)-3,4-dihydroquinolin-6-yl]methyl]benzenesulfonamide (Compound 11.001)

6-(Aminomethyl)-1-(2,2,2-trifluoroethyl)-3,4-dihydroquinolin-2-one hydrochloride (0.150 g, 0.509 mmol) was suspend in ethyl acetate (5 mL) and N-ethyl-N-isopropylpropan-2-amine (0.218 mL, 1.27 mmol) was added dropwise. Then benzenesulfonyl chloride (0.102 g, 0.560 mmol) was added dropwise and the reaction mixture was stirred for 3 h at room temperature. The solvent were removed under vacuum and the crude compound was purified on silica gel to give N-[2-oxo-1-(2,2,2-trifluoroethyl)-3,4-dihydroquinolin-6-yl]methyl]benzenesulfonamide (144 mg, 71%) of a pale yellow solid. $^1$H NMR (400 MHz, CHLOROFORM-d) δ ppm 1.26 (t, 1H), 2.05 (s, 1H), 2.61-2.72 (m, 2H), 2.82-2.91 (m, 2H), 4.04-4.17 (m, 2H), 4.04-4.19 (m, 3H), 4.61 (q, 2H), 5.03 (t, 1H), 6.94 (d, 1H), 7.01-7.06 (m, 1H), 7.07-7.16 (m, 1H), 7.47-7.54 (m, 2H), 7.55-7.66 (m, 1H), 7.86 (d, 2H); LC-MS (Method A): RT 0.92, (399, M+H$^+$).

Example P6: Preparation of N-[[2-oxo-1-(3-pyridyl)-3,4-dihydroquinolin-6-yl]methyl]benzenesulfonamide 9.001

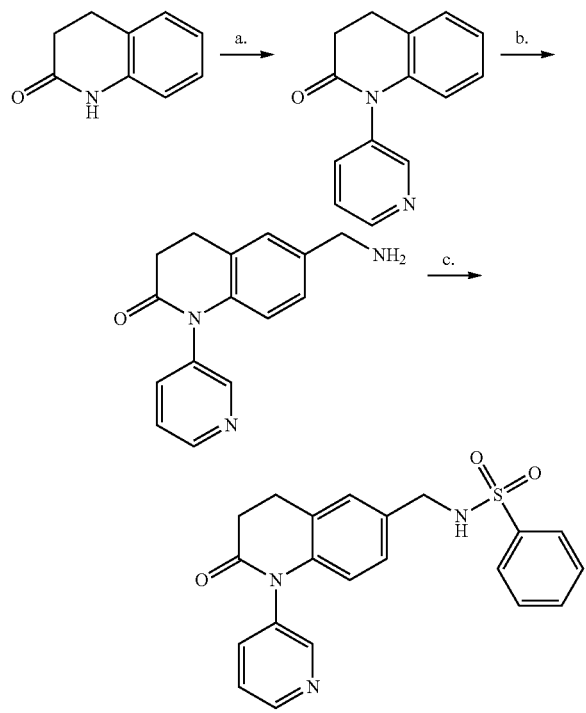

a. 1-(3-pyridyl)-3,4-dihydroquinolin-2-one

Under Argon, 3,4-dihydro-1H-quinolin-2-one (0.736 g, 5.00 mmol), cesium carbonate (4.14 g, 12.5 mmol), copper Iodide (0.145, 1 mmol) and ethyl 2-oxocyclohexanecarboxylate (0,426 g, 2.25 mmol) were added. Then 3-iodopyridine (1.13 g, 5.5 mmol) in dimethylsulfoxide (5 mL) was added, and the reaction mixture was heated at 110° C. for 3 h. The mixture was poured into 20 mL of ice-water, the water-phase was extracted with ethyl acetate and the combined organic phases were washed with water and brine, dried with Na$_2$SO$_4$, filtrated and concentrated. The crude product was purified on silica gel to give 1-(3-pyridyl)-3,4-dihydroquinolin-2-one (746 mg, 3.32 mmol, 66.5%). $^1$H NMR (400 MHz, CDCl$_3$) δ ppm 2.82-2.89 (m, 2H), 3.06-3.13 (m, 2H), 6.34 (d, 1H), 7.00-7.10 (m, 2H), 7.24 (d, 1H), 7.46 (dd, 1H), 7.64 (dt, 1H), 8.52 (d, 1H), 8.66 (dd, 1H); LC-MS (Method A): RT 0.72, (225, M+H$^+$).

b. 6-(aminomethyl)-1-(3-pyridyl)-3,4-dihydroquinolin-2-one 1-(3-Pyridyl)-3,4-dihydroquinolin-2-one (312 mg, 1.39 mmol) in acetic acid (5 mL) was dissolved in sulfuric acid (1.5 mL), then 2chloro-N-(hydroxymethyl)acetamide (0.171 g, 1.39 mmol) was added, reaction mixture was stirred at room temperature for 2 hours at 50° C. Ice water and a solution of potassium carbonate were added, the water phase was extracted with ethyl acetate, and the organic phase was dried and concentrated on vacuum. The crude product was purified by flash chromatography to give 2-chloro-N-[[2-oxo-1-(3-pyridyl)-3,4-dihydroquinolin-6-yl]methyl]acetamide (177 mg, 38%); H NMR (400 MHz, CDCl$_3$) δ ppm 2.84 (dd, 2H), 3.05-3.13 (m, 2H), 4.06-4.13 (m, 2H), 4.43 (d, 2H), 6.32 (d, 1H), 6.90 (br. s., 1H), 6.99 (d, 1H), 7.19 (s, 1H), 7.47 (dd, 1H), 7.62 (dt, 1H), 8.50 (d, 1H), 8.67 (dd, 1H); LC-MS (Method A): RT 0.62, (328, M–H$^+$), (329, M+H$^+$).

2-Chloro-N-[[2-oxo-1-(3-pyridyl)-3,4-dihydroquinolin-6-yl]methyl]acetamide (167 mg, 0.506 mmol) in ethanol (1.25 mL) was added hydrochloride acid (1.25 mL). Reaction mixture was stirred over night at 90-95° C. Ethanol (10 mL) was added at this mixture and the precipitate was filtered then washed with ethyl ether to give 6-(aminomethyl)-1-(3-pyridyl)-3,4-dihydroquinolin-2-one dihydrochloride (155 mg, 93%) which was used directly for the next step; LC-MS (Method A): RT 0.22, (254, M+H$^+$).

c. Preparation of N-[[2-oxo-1-(3-pyridyl)-3,4-dihydroquinolin-6-yl]methyl]benzenesulfonamide (Compound 9.001)

6-(Aminomethyl)-1-(3-pyridyl)-3,4-dihydroquinolin-2-one dihydrochloride (0.163 g, 0.50 mmol) was suspend in ethyl acetate (6.5 mL) with diisopropylethylamine (0.226 g, 1.75 mmol) and stirred at room temperature during 15 min. Benzenesulfonyl chloride (0.115 g, 0.65 mmol) was added and reaction mixture was stirred over the weekend at room temperature. Water was added and extracted two times with ethyl acetate. The combined organic phases were washed with a solution of sodium hydrogen carbonate, dried and concentrated to give N-[[2-oxo-1-(3-pyridyl)-3,4-dihydroquinolin-6-yl]methyl]benzenesulfonamide (48 mg, 24%) after a purification by flash chromatography. H NMR (400 MHz, CDCl$_3$) δ ppm 2.76-2.85 (m, 2H), 2.98-3.05 (m, 2H), 4.06-4.13 (m, 2H), 4.83 (t, 1H), 6.23 (d, 1H), 6.88 (d, 1H), 7.11 (s, 1H), 7.46 (dd, 1H), 7.49-7.56 (m, 2H), 7.60 (d, 2H), 7.87 (d, 2H), 8.42 (d, 1H), 8.66 (d, J=3.67 Hz, 1H); LC-MS (Method A): RT 0.79, (392, M–H⁺), (394, M+H⁺).

Compounds of the present invention were made using these methods, as shown in the table below.

| Compound | Name | RT (min) | [M + H] (measured) | Method | MP (° C.) |
|---|---|---|---|---|---|
| 2.024 | N-[(1-ethyl-2-oxo-3,4-dihydroquinolin-6-yl)methyl]-1-(p-tolyl)methanesulfonamide | 0.91 | 373 | A | |
| 3.024 | N-[(2-oxo-1-propyl-3,4-dihydroquinolin-6-yl)methyl]-1-(p-tolyl)methanesulfonamide | 0.96 | 387 | A | |
| 2.015 | N-[(1-ethyl-2-oxo-3,4-dihydroquinolin-6-yl)methyl]-4-(trifluoromethyl)benzenesulfonamide | 0.94 | 413 | A | 180-181 |
| 2.012 | N-[(1-ethyl-2-oxo-3,4-dihydroquinolin-6-yl)methyl]-4-methyl-benzenesulfonamide | 0.89 | 359 | A | 202-203 |
| 3.012 | 4-methyl-N-[(2-oxo-1-propyl-3,4-dihydroquinolin-6-yl)methyl]benzenesulfonamide | 0.94 | 373 | A | 153-154 |
| 3.015 | N-[(2-oxo-1-propyl-3,4-dihydroquinolin-6-yl)methyl]-4-(trifluoromethyl)benzenesulfonamide | 0.99 | 427 | A | 138-140 |
| 2.006 | N-[(1-ethyl-2-oxo-3,4-dihydroquinolin-6-yl)methyl]-2,4-difluoro-benzenesulfonamide | 0.86 | 381 | A | 167-168 |
| 2.009 | N-[(1-ethyl-2-oxo-3,4-dihydroquinolin-6-yl)methyl]-4-fluoro-benzenesulfonamide | 0.85 | 363 | A | 190-191 |
| 2.017 | 2-bromo-N-[(1-ethyl-2-oxo-3,4-dihydroquinolin-6-yl)methyl]benzenesulfonamide | 0.87 | 425 | A | 206-207 |
| 2.011 | N-[(1-ethyl-2-oxo-3,4-dihydroquinolin-6-yl)methyl]-2-methyl-benzenesulfonamide | 0.88 | 359 | A | 203-206 |
| 2.014 | N-[(1-ethyl-2-oxo-3,4-dihydroquinolin-6-yl)methyl]-2,4-dimethyl-benzenesulfonamide | 0.93 | 373 | A | 199-200 |
| 2.001 | N-[(1-ethyl-2-oxo-3,4-dihydroquinolin-6-yl)methyl]benzenesulfonamide | 0.84 | 346 | A | 114-124 |
| 2.010 | N-[(1-ethyl-2-oxo-3,4-dihydroquinolin-6-yl)methyl]-4-methoxy-benzenesulfonamide | 0.85 | 375 | A | 147-150 |
| 2.007 | N-[(1-ethyl-2-oxo-3,4-dihydroquinolin-6-yl)methyl]-2-fluoro-benzenesulfonamide | 0.84 | 364 | A | 155-163 |
| 2.002 | 4-bromo-N-[(1-ethyl-2-oxo-3,4-dihydroquinolin-6-yl)methyl]benzenesulfonamide | | | | 176-183 |
| 3.006 | 2,4-difluoro-N-[(2-oxo-1-propyl-3,4-dihydroquinolin-6-yl)methyl]benzenesulfonamide | 0.91 | 395 | A | 141-144 |
| 3.005 | 2,6-difluoro-N-[(2-oxo-1-propyl-3,4-dihydroquinolin-6-yl)methyl]benzenesulfonamide | 0.88 | 395 | A | 182-183 |
| 3.009 | 4-fluoro-N-[(2-oxo-1-propyl-3,4-dihydroquinolin-6-yl)methyl]benzenesulfonamide | 0.9 | 377 | A | 143-144 |
| 3.007 | 2-fluoro-N-[(2-oxo-1-propyl-3,4-dihydroquinolin-6-yl)methyl]benzenesulfonamide | 0.89 | 377 | A | 155-156 |
| 3.001 | N-[(2-oxo-1-propyl-3,4-dihydroquinolin-6-yl)methyl]benzenesulfonamide | 0.89 | 359 | A | 159-161 |
| 3.011 | 2-methyl-N-[(2-oxo-1-propyl-3,4-dihydroquinolin-6-yl)methyl]benzenesulfonamide | 0.93 | 373 | A | 163-165 |
| 3.004 | 4-chloro-N-[(2-oxo-1-propyl-3,4-dihydroquinolin-6-yl)methyl]benzenesulfonamide | 0.95 | 393 | A | 138-139 |
| 3.010 | 4-methoxy-N-[(2-oxo-1-propyl-3,4-dihydroquinolin-6-yl)methyl]benzenesulfonamide | 0.9 | 390 | A | 143-144 |
| 3.014 | 2,4-dimethyl-N-[(2-oxo-1-propyl-3,4-dihydroquinolin-6-yl)methyl]benzenesulfonamide | 0.98 | 388 | A | 166-167 |
| 3.017 | 2-bromo-N-[(2-oxo-1-propyl-3,4-dihydroquinolin-6-yl)methyl]benzenesulfonamide | 0.93 | 439 | A | 157-159 |
| 3.016 | 4-isopropoxy-N-[(2-oxo-1-propyl-3,4-dihydroquinolin-6-yl)methyl]benzenesulfonamide | 0.99 | 417 | A | 138-139 |
| 3.002 | 4-bromo-N-[(2-oxo-1-propyl-3,4-dihydroquinolin-6-yl)methyl]benzenesulfonamide | 0.96 | 439 | A | 143-145 |
| 3.023 | 1-(2-fluorophenyl)-N-[(2-oxo-1-propyl-3,4-dihydroquinolin-6-yl)methyl]methanesulfonamide | 1.41 | 391 | B | |
| 3.025 | 1-(2,4-difluorophenyl)-N-[(2-oxo-1-propyl-3,4-dihydroquinolin-6-yl)methyl]methanesulfonamide | 1.44 | 409 | B | |
| 3.026 | 1-(2,6-difluorophenyl)-N-[(2-oxo-1-propyl-3,4-dihydroquinolin-6-yl)methyl]methanesulfonamide | 1.42 | 409 | B | |
| 3.036 | 1-(4-bromo-2-fluoro-phenyl)-N-[(2-oxo-1-propyl-3,4-dihydroquinolin-6-yl)methyl]methanesulfonamide | 1.58 | 469 | B | |
| 3.037 | 1-(2,5-difluorophenyl)-N-[(2-oxo-1-propyl-3,4-dihydroquinolin-6-yl)methyl]methanesulfonamide | 1.43 | 409 | B | |
| 3.038 | 1-(2,3-difluorophenyl)-N-[(2-oxo-1-propyl-3,4-dihydroquinolin-6-yl)methyl]methanesulfonamide | 1.44 | 409 | B | |
| 3.039 | 1-(2-bromo-4-fluoro-phenyl)-N-[(2-oxo-1-propyl-3,4-dihydroquinolin-6-yl)methyl]methanesulfonamide | 1.55 | 469 | B | |
| 3.040 | 1-(2-bromo-4-chloro-phenyl)-N-[(2-oxo-1-propyl-3,4-dihydroquinolin-6-yl)methyl]methanesulfonamide | 1.66 | 485 | B | |
| 3.041 | 1-(4-cyanophenyl)-N-[(2-oxo-1-propyl-3,4-dihydroquinolin-6-yl)methyl]methanesulfonamide | 1.3 | 398 | B | |
| 3.042 | 1-(4-cyano-2-fluoro-phenyl)-N-[(2-oxo-1-propyl-3,4-dihydroquinolin-6-yl)methyl]methanesulfonamide | 1.35 | 416 | B | |

| Compound | Name | RT (min) | [M + H] (measured) | Method | MP (° C.) |
|---|---|---|---|---|---|
| 3.043 | 1-(2-cyanophenyl)-N-[(2-oxo-1-propyl-3,4-dihydroquinolin-6-yl)methyl]methanesulfonamide | 1.31 | 398 | B | |
| 3.044 | 1-(2-chloro-4-fluoro-phenyl)-N-[(2-oxo-1-propyl-3,4-dihydroquinolin-6-yl)methyl]methanesulfonamide | 1.49 | 425 | B | |
| 3.045 | 1-(4-tert-butylphenyl)-N-[(2-oxo-1-propyl-3,4-dihydroquinolin-6-yl)methyl]methanesulfonamide | 1.77 | 429 | B | |
| 3.046 | N-[(2-oxo-1-propyl-3,4-dihydroquinolin-6-yl)methyl]-1-[4-(trifluoromethoxy)phenyl]methanesulfonamide | 1.62 | 457 | B | |
| 3047 | N-[(2-oxo-1-propyl-3,4-dihydroquinolin-6-yl)methyl]-1-[4-(trifluoromethyl)phenyl]methanesulfonamide | 1.58 | 441 | B | |
| 3.033 | N-[(2-oxo-1-propyl-3,4-dihydroquinolin-6-yl)methyl]-1-[3-(trifluoromethyl)phenyl]methanesulfonamide | 1.57 | 441 | B | |
| 3.031 | 1-(4-chlorophenyl)-N-[(2-oxo-1-propyl-3,4-dihydroquinolin-6-yl)methyl]methanesulfonamide | 1.51 | 407 | B | |
| 3.050 | N-[(2-oxo-1-propyl-3,4-dihydroquinolin-6-yl)methyl]-1-[4-(trifluoromethylsulfanyl)phenyl]methanesulfonamide | 1.7 | 473 | B | |
| 3.032 | N-[(2-oxo-1-propyl-3,4-dihydroquinolin-6-yl)methyl]-1-[6-(trifluoromethyl)-3-pyridyl]methanesulfonamide | 1.4 | 442 | B | |
| 3.022 | 1-(2-bromophenyl)-N-[(2-oxo-1-propyl-3,4-dihydroquinolin-6-yl)methyl]methanesulfonamide | 1.52 | 451 | B | |
| 3.035 | N-[(2-oxo-1-propyl-3,4-dihydroquinolin-6-yl)methyl]-2-phenyl-ethanesulfonamide | 1.45 | 387 | B | |
| 3.030 | 1-(3-fluorophenyl)-N-[(2-oxo-1-propyl-3,4-dihydroquinolin-6-yl)methyl]methanesulfonamide | 1.41 | 391 | B | |
| 3.029 | 1-(2,4-dichlorophenyl)-N-[(2-oxo-1-propyl-3,4-dihydroquinolin-6-yl)methyl]methanesulfonamide | 1.64 | 441 | B | |
| 3.049 | 1-(3-bromophenyl)-N-[(2-oxo-1-propyl-3,4-dihydroquinolin-6-yl)methyl]methanesulfonamide | 1.53 | 451 | B | |
| 3.028 | 1-(4-nitrophenyl)-N-[(2-oxo-1-propyl-3,4-dihydroquinolin-6-yl)methyl]methanesulfonamide | 1.38 | 418 | B | |
| 3.022 | 1-(4-bromophenyl)-N-[(2-oxo-1-propyl-3,4-dihydroquinolin-6-yl)methyl]methanesulfonamide | 1.54 | 451 | B | |
| 3.034 | methyl 3-[(2-oxo-1-propyl-3,4-dihydroquinolin-6-yl)methylsulfamoyl]propanoate | 1.13 | 369 | B | |
| 3.021 | N-[(2-oxo-1-propyl-3,4-dihydroquinolin-6-yl)methyl]-1-phenyl-methanesulfonamide | 1.38 | 373 | B | |
| 3.019 | N-[(2-oxo-1-propyl-3,4-dihydroquinolin-6-yl)methyl]butane-1-sulfonamide | 1.34 | 339 | B | |
| 3.018 | N-[(2-oxo-1-propyl-3,4-dihydroquinolin-6-yl)methyl]cyclopropanesulfonamide | 1.15 | 323 | B | |
| 2.023 | N-[(1-ethyl-2-oxo-3,4-dihydroquinolin-6-yl)methyl]-1-(2-fluorophenyl)methanesulfonamide | 1.29 | 377 | B | |
| 2.025 | 1-(2,4-difluorophenyl)-N-[(1-ethyl-2-oxo-3,4-dihydroquinolin-6-yl)methyl]methanesulfonamide | 1.33 | 395 | B | |
| 2.026 | 1-(2,6-difluorophenyl)-N-[(1-ethyl-2-oxo-3,4-dihydroquinolin-6-yl)methyl]methanesulfonamide | 1.31 | 395 | B | |
| 2.036 | 1-(4-bromo-2-fluoro-phenyl)-N-[(1-ethyl-2-oxo-3,4-dihydroquinolin-6-yl)methyl]methanesulfonamide | 1.47 | 455 | B | |
| 2.037 | 1-(2,5-difluorophenyl)-N-[(1-ethyl-2-oxo-3,4-dihydroquinolin-6-yl)methyl]methanesulfonamide | 1.32 | 395 | B | |
| 2.038 | 1-(2,3-difluorophenyl)-N-[(1-ethyl-2-oxo-3,4-dihydroquinolin-6-yl)methyl]methanesulfonamide | 1.33 | 395 | B | |
| 2.039 | 1-(2-bromo-4-fluoro-phenyl)-N-[(1-ethyl-2-oxo-3,4-dihydroquinolin-6-yl)methyl]methanesulfonamide | 1.57 | 455 | B | |
| 2.040 | 1-(2-bromo-4-chloro-phenyl)-N-[(1-ethyl-2-oxo-3,4-dihydroquinolin-6-yl)methyl]methanesulfonamide | 1.56 | 471 | B | |
| 2.041 | 1-(2-cyanophenyl)-N-[(1-ethyl-2-oxo-3,4-dihydroquinolin-6-yl)methyl]methanesulfonamide | 1.2 | 384 | B | |
| 2.042 | 1-(2-chloro-4-fluoro-phenyl)-N-[(1-ethyl-2-oxo-3,4-dihydroquinolin-6-yl)methyl]methanesulfonamide | 1.39 | 411 | B | |
| 2.045 | 1-(4-tert-butylphenyl)-N-[(1-ethyl-2-oxo-3,4-dihydroquinolin-6-yl)methyl]methanesulfonamide | 1.68 | 415 | B | |
| 2.046 | N-[(1-ethyl-2-oxo-3,4-dihydroquinolin-6-yl)methyl]-1-[4-(trifluoromethoxy)phenyl]methanesulfonamide | 1.53 | 443 | B | |
| 2.047 | N-[(1-ethyl-2-oxo-3,4-dihydroquinolin-6-yl)methyl]-1-[4-(trifluoromethyl)phenyl]methanesulfonamide | 1.49 | 427 | B | |
| 2.033 | N-[(1-ethyl-2-oxo-3,4-dihydroquinolin-6-yl)methyl]-1-[3-(trifluoromethyl)phenyl]methanesulfonamide | 1.48 | 427 | B | |
| 2.031 | 1-(4-chlorophenyl)-N-[(1-ethyl-2-oxo-3,4-dihydroquinolin-6-yl)methyl]methanesulfonamide | 1.41 | 393 | B | |
| 2.032 | N-[(1-ethyl-2-oxo-3,4-dihydroquinolin-6-yl)methyl]-1-[6-(trifluoromethyl)-3-pyridyl]methanesulfonamide | 1.29 | 428 | B | |
| 2.048 | 1-(2-bromophenyl)-N-[(1-ethyl-2-oxo-3,4-dihydroquinolin-6-yl)methyl]methanesulfonamide | 1.41 | 437 | B | |
| 2.035 | N-[(1-ethyl-2-oxo-3,4-dihydroquinolin-6-yl)methyl]-2-phenyl-ethanesulfonamide | 1.34 | 373 | B | |

-continued

| Compound | Name | RT (min) | [M + H] (measured) | Method | MP (° C.) |
|---|---|---|---|---|---|
| 2.030 | N-[(1-ethyl-2-oxo-3,4-dihydroquinolin-6-yl)methyl]-1-(3-fluorophenyl)methanesulfonamide | 1.3 | 377 | B | |
| 2.029 | 1-(2,4-dichlorophenyl)-N-[(1-ethyl-2-oxo-3,4-dihydroquinolin-6-yl)methyl]methanesulfonamide | 1.54 | 427 | B | |
| 2.049 | 1-(3-bromophenyl)-N-[(1-ethyl-2-oxo-3,4-dihydroquinolin-6-yl)methyl]methanesulfonamide | 1.43 | 437 | B | |
| 2.022 | 1-(4-bromophenyl)-N-[(1-ethyl-2-oxo-3,4-dihydroquinolin-6-yl)methyl]methanesulfonamide | 1.44 | 437 | B | |
| 2.034 | methyl 3-[(1-ethyl-2-oxo-3,4-dihydroquinolin-6-yl)methylsulfamoyl]propanoate | 1.01 | 355 | B | |
| 2.021 | N-[(1-ethyl-2-oxo-3,4-dihydroquinolin-6-yl)methyl]-1-phenyl-methanesulfonamide | 1.27 | 359 | B | |
| 2.019 | N-[(1-ethyl-2-oxo-3,4-dihydroquinolin-6-yl)methyl]butane-1-sulfonamide | 1.22 | 325 | B | |
| 3.027 | 1-(4-cyclopropylphenyl)-N-[(2-oxo-1-propyl-3,4-dihydroquinolin-6-yl)methyl]methanesulfonamide | 1.7 | 413 | B | |
| 2.027 | 1-(4-cyclopropylphenyl)-N-[(1-ethyl-2-oxo-3,4-dihydroquinolin-6-yl)methyl]methanesulfonamide | 1.6 | 399 | B | |
| 3.051 | (E)-N-[(2-oxo-1-propyl-3,4-dihydroquinolin-6-yl)methyl]-2-phenyl-ethenesulfonamide | 0.94 | 385 | A | 165-168 |
| 3.053 | (E)-2-(4-chlorophenyl)-N-[(2-oxo-1-propyl-3,4-dihydroquinolin-6-yl)methyl]methenesulfonamide | 1.00 | 419 | A | 153-154 |
| 3.056 | (E)-2-(2-fluorophenyl)-N-[(2-oxo-1-propyl-3,4-dihydroquinolin-6-yl)methyl]ethenesulfonamide | 0.95 | 403 | A | 139-173 |
| 2.051 | (E)-N-[(1-ethyl-2-oxo-3,4-dihydroquinolin-6-yl)methyl]-2-phenyl-ethenesulfonamide | 0.88 | 371 | A | 134-137 |
| 3.060 | (E)-N-[(2-oxo-1-propyl-6-quinolyl)methyl]prop-1-ene-1-sulfonamide | 0.83 | 323 | A | 95-99 |
| 3.020 | 4,4,4-trifluoro-N-[(2-oxo-1-propyl-3,4-dihydroquinolin-6-yl)methyl]butane-1-sulfonamide | 0.90 | 393 | A | |
| 3.061 | 5-methyl-N-[(2-oxo-1-propyl-3,4-dihydroquinolin-6-yl)methyl]thiophene-2-sulfonamide | 0.95 | 379 | A | 151-154 |
| 2.059 | (E)-N-[(1-ethyl-2-oxo-3,4-dihydroquinolin-6-yl)methyl]-2-(p-tolyl)ethenesulfonamide | 0.93 | 385 | A | 151-153 |
| 2.062 | N-[(1-ethyl-2-oxo-3,4-dihydroquinolin-6-yl)methyl]propane-1-sulfonamide | 0.8 | 311 | A | |
| 3.063 | 1-methyl-N-[(2-oxo-1-propyl-3,4-dihydroquinolin-6-yl)methyl]imidazole-4-sulfonamide | 0.73 | 363 | A | 168-171 |
| 2.063 | N-[(1-ethyl-2-oxo-3,4-dihydroquinolin-6-yl)methyl]-1-methyl-imidazole-4-sulfonamide | 0.63 | 349 | A | 165-167 |
| 2.064 | 2,5-dichloro-N-[(1-ethyl-2-oxo-3,4-dihydroquinolin-6-yl)methyl]thiophene-3-sulfonamide | 0.94 | 421 | A | 198-201 |
| 2.018 | N-[(1-ethyl-2-oxo-3,4-dihydroquinolin-6-yl)methyl]cyclopropanesulfonamide | 0.75 | 309 | A | 104-106 |
| 3.059 | (E)-N-[(2-oxo-1-propyl-3,4-dihydroquinolin-6-yl)methyl]-2-(p-tolyl)ethenesulfonamide | 0.97 | 399 | A | 172-174 |
| 3.052 | (E)-2-(4-bromophenyl)-N-[(2-oxo-1-propyl-3,4-dihydroquinolin-6-yl)methyl]ethenesulfonamide | 1.01 | 465 | A | 150-152 |
| 3.066 | (E)-N-[(2-oxo-1-propyl-3,4-dihydroquinolin-6-yl)methyl]but-2-ene-1-sulfonamide | 0.88 | 337 | A | |
| 2.060 | (E)-N-[(1-ethyl-2-oxo-3,4-dihydroquinolin-6-yl)methyl]prop-1-ene-1-sulfonamide | 0.78 | 309 | A | |
| 3.062 | N-[(2-oxo-1-propyl-3,4-dihydroquinolin-6-yl)methyl]propane-1-sulfonamide | 0.85 | 325 | A | |
| 2.067 | N-[(1-ethyl-2-oxo-3,4-dihydroquinolin-6-yl)methyl]-3,3,3-trifluoro-propane-1-sulfonamide | 0.86 | 365 | A | |
| 3.067 | 3,3,3-trifluoro-N-[(2-oxo-1-propyl-3,4-dihydroquinolin-6-yl)methyl]propane-1-sulfonamide | 0.91 | 379 | A | 132-135 |
| 2.068 | N-[(1-ethyl-2-oxo-3,4-dihydroquinolin-6-yl)methyl]thiophene-3-sulfonamide | 0.85 | 351 | A | 128-131 |
| 3.068 | N-[(2-oxo-1-propyl-3,4-dihydroquinolin-6-yl)methyl]thiophene-3-sulfonamide | 0.88 | 365 | A | 150-154 |
| 2.052 | (E)-2-(4-bromophenyl)-N-[(1-ethyl-2-oxo-3,4-dihydroquinolin-6-yl)methyl]ethenesulfonamide | 0.96 | 451 | A | 119-124 |
| 2.069 | (E)-2-(3-chlorophenyl)-N-[(1-ethyl-2-oxo-3,4-dihydroquinolin-6-yl)methyl]ethenesulfonamide | 0.93 | 405 | A | 149-151 |
| 2.020 | N-[(1-ethyl-2-oxo-3,4-dihydroquinolin-6-yl)methyl]-4,4,4-trifluoro-butane-1-sulfonamide | 0.85 | 379 | A | |
| 2.070 | (E)-2-(3-bromophenyl)-N-[(1-ethyl-2-oxo-3,4-dihydroquinolin-6-yl)methyl]ethenesulfonamide | 0.97 | 451 | A | 144-147 |
| 3.069 | (E)-2-(3-chlorophenyl)-N-[(2-oxo-1-propyl-3,4-dihydroquinolin-6-yl)methyl]ethenesulfonamide | 0.98 | 419 | A | 129-133 |
| 3.070 | (E)-2-(3-bromophenyl)-N-[(2-oxo-1-propyl-3,4-dihydroquinolin-6-yl)methyl]ethenesulfonamide | 1.00 | 465 | A | 148-153 |
| 3.060 | (E)-N-[(2-oxo-1-propyl-3,4-dihydroquinolin-6-yl)methyl]prop-1-ene-1-sulfonamide | 0.84 | 323 | A | 95-99 |

-continued

| Compound | Name | RT (min) | [M + H] (measured) | Method | MP (° C.) |
|---|---|---|---|---|---|
| 3.020 | 4,4,4-trifluoro-N-[(2-oxo-1-propyl-3,4-dihydroquinolin-6-yl)methyl]butane-1-sulfonamide | 0.91 | 393 | A | |
| 3.056 | (E)-2-(2-fluorophenyl)-N-[(2-oxo-1-propyl-3,4-dihydroquinolin-6-yl)methyl]ethenesulfonamide | 0.95 | 403 | A | 169-173 |
| 2.051 | (E)-N-[(1-ethyl-2-oxo-3,4-dihydroquinolin-6-yl)methyl]-2-phenyl-ethenesulfonamide | 0.87 | 371 | A | 134-137 |
| 2.061 | N-[(1-ethyl-2-oxo-3,4-dihydroquinolin-6-yl)methyl]-5-methyl-thiophene-2-sulfonamide | 0.87 | 365 | A | 149-152 |
| 3.064 | 2,5-dichloro-N-[(2-oxo-1-propyl-3,4-dihydroquinolin-6-yl)methyl]thiophene-3-sulfonamide | 1.00 | 433 | A | 131-134 |
| 3.071 | N-[(2-oxo-1-propyl-3,4-dihydroquinolin-6-yl)methyl]prop-2-ene-1-sulfonamide | 0.80 | 323 | A | |
| 16.001 | N-[(1-ethyl-4,8-dimethyl-2-oxo-3,4-dihydroquinolin-6-yl)methyl]benzenesulfonamide | 0.93 | 373 | A | |
| 9.001 | N-[[2-oxo-1-(3-pyridyl)-3,4-dihydroquinolin-6-yl]methyl]benzenesulfonamide | 0.78 | 394 | A | |
| 8.001 | N-[(2-oxo-1-phenyl-3,4-dihydroquinolin-6-yl)methyl]benzenesulfonamide | 0.91 | 393 | A | |
| 8.006 | 2,4-difluoro-N-[(2-oxo-1-phenyl-3,4-dihydroquinolin-6-yl)methyl]benzenesulfonamide | 0.94 | 429 | A | |
| 7.009 | 4-fluoro-N-[(2-oxo-1-propyl-6-quinolyl)methyl]benzenesulfonamide | 0.86 | 376 | A | |
| 7.001 | 2,4-difluoro-N-[(2-oxo-1-propyl-6-quinolyl)methyl]benzenesulfonamide | 0.85 | 357 | A | |
| 7.006 | 2,4-difluoro-N-[(2-oxo-1-propyl-6-quinolyl)methyl]benzenesulfonamide | 0.88 | 393 | A | |
| 13.006 | 2,4-difluoro-N-[[1-(2-methoxyethyl)-2-oxo-3,4-dihydroquinolin-6-yl]methyl]benzenesulfonamide | 0.86 | 411 | A | |
| 13.001 | N-[[1-(2-methoxyethyl)-2-oxo-3,4-dihydroquinolin-6-yl]methyl]benzenesulfonamide | 0.83 | 375 | A | |
| 5.006 | N-[(1-allyl-2-oxo-3,4-dihydroquinolin-6-yl)methyl]-2,4-difluoro-benzenesulfonamide | 0.9 | 393 | A | |
| 5.001 | N-[(1-allyl-2-oxo-3,4-dihydroquinolin-6-yl)methyl]benzenesulfonamide | 0.88 | 357 | A | |
| 11.006 | 2,4-difluoro-N-[[2-oxo-1-(2,2,2-trifluoroethyl)-3,4-dihydroquinolin-6-yl]methyl]benzenesulfonamide | 0.94 | 435 | A | |
| 11.001 | N-[[2-oxo-1-(2,2,2-trifluoroethyl)-3,4-dihydroquinolin-6-yl]methyl]benzenesulfonamide | 0.92 | 399 | A | |
| 10.006 | N-[[1-(cyclopropylmethyl)-2-oxo-3,4-dihydroquinolin-6-yl]methyl]-2,4-difluoro-benzenesulfonamide | 0.94 | 407 | A | |
| 10.001 | N-[[1-(cyclopropylmethyl)-2-oxo-3,4-dihydroquinolin-6-yl]methyl]benzenesulfonamide | 0.92 | 371 | A | |
| 22.001 | N-[(1-ethyl-8-fluoro-4-methyl-2-oxo-3,4-dihydroquinolin-6-yl)methyl]benzenesulfonamide | 0.91 | 377 | A | |
| 3.073 | 5-chloro-N-[(2-oxo-1-propyl-3,4-dihydroquinolin-6-yl)methyl]thiophene-2-sulfonamide | 0.97 | 399 | A | 144-147 |
| 3.072 | N-[(2-oxo-1-propyl-3,4-dihydroquinolin-6-yl)methyl]thiophene-2-sulfonamide | 0.88 | 365 | A | 151-153 |
| 17.001 | N-[(8-fluoro-2-oxo-1-propyl-3,4-dihydroquinolin-6-yl)methyl]benzenesulfonamide | 0.93 | 377 | A | |
| 3.074 | N-[(2-oxo-1-propyl-3,4-dihydroquinolin-6-yl)methyl]naphthalene-1-sulfonamide | 0.96 | 409 | A | 176-179 |
| 3.075 | N-[(2-oxo-1-propyl-3,4-dihydroquinolin-6-yl)methyl]naphthalene-2-sulfonamide | 0.96 | 409 | A | 169-173 |
| 14.006 | 2,4-difluoro-N-[1-(2-oxo-1-propyl-3,4-dihydroquinolin-6-yl)ethyl]benzenesulfonamide | 0.95 | 409 | A | |
| 14.009 | 4-fluoro-N-[1-(2-oxo-1-propyl-3,4-dihydroquinolin-6-yl)ethyl]benzenesulfonamide | 0.94 | 391 | A | |
| 14.001 | N-[1-(2-oxo-1-propyl-3,4-dihydroquinolin-6-yl)ethyl]benzenesulfonamide | 0.93 | 373 | A | |
| 15.006 | 2,4-difluoro-N-[1-(2-oxo-1-propyl-3,4-dihydroquinolin-6-yl)cyclopropyl]benzenesulfonamide | 0.96 | 421 | A | |
| 15.009 | 4-fluoro-N-[1-(2-oxo-1-propyl-3,4-dihydroquinolin-6-yl)cyclopropyl]benzenesulfonamide | 0.95 | 403 | A | |
| 15.001 | N-[1-(2-oxo-1-propyl-3,4-dihydroquinolin-6-yl)cyclopropyl]benzenesulfonamide | 0.93 | 385 | A | |
| 20.006 | N-[(1-ethyl-4-methyl-2-oxo-3,4-dihydroquinolin-6-yl)methyl]-2,4-difluoro-benzenesulfonamide | 0.95 | 395 | A | |
| 20.001 | N-[(1-ethyl-4-methyl-2-oxo-3,4-dihydroquinolin-6-yl)methyl]benzenesulfonamide | 0.87 | 359 | A | |
| 23.001 | N-[[4-methyl-2-oxo-1-(2,2,2-trifluoroethyl)-3,4-dihydroquinolin-6-yl]methyl]benzenesulfonamide | 0.95 | 413 | A | |
| 23.006 | 2,4-difluoro-N-[[4-methyl-2-oxo-1-(2,2,2-trifluoroethyl)-3,4-dihydroquinolin-6-yl]methyl]benzenesulfonamide | 0.97 | 449 | A | |
| 24.001 | N-[[1-(cyclopropylmethyl)-4-methyl-2-oxo-3,4-dihydroquinolin-6-yl]methyl]benzenesulfonamide | 0.96 | 385 | A | |

-continued

| Compound | Name | RT (min) | [M + H] (measured) | Method | MP (° C.) |
|---|---|---|---|---|---|
| 24.006 | N-[[1-(cyclopropylmethyl)-4-methyl-2-oxo-3,4-dihydroquinolin-6-yl]methyl]-2,4-difluoro-benzenesulfonamide | 0.98 | 421 | A | |
| 25.001 | N-[(1-allyl-4-methyl-2-oxo-3,4-dihydroquinolin-6-yl)methyl]benzenesulfonamide | 0.92 | 371 | A | |
| 25.006 | N-[(1-allyl-4-methyl-2-oxo-3,4-dihydroquinolin-6-yl)methyl]-2,4-difluoro-benzenesulfonamide | 0.92 | 407 | A | |
| 26.001 | N-[(7-fluoro-2-oxo-1-propyl-3,4-dihydroquinolin-6-yl)methyl]benzenesulfonamide | 0.93 | 377 | A | |
| 27.001 | N-[(5-fluoro-2-oxo-1-propyl-3,4-dihydroquinolin-6-yl)methyl]benzenesulfonamide | 0.92 | 377 | A | |

Method—A:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 0% B, 100% A; 1.2-1.5 min 100% B; Flow (ml/min) 0.85

Method—B:

Spectra were recorded on a Mass Spectrometer from Waters SQD 2 equipped with an electrospray source (Polarity: positive ions, Capillary: 3.5 kV, Cone range: 30 V, Extractor: 3.00 V, Source Temperature: 150° C., Desolvation Temperature: 400° C., Cone Gas Flow: 60 L/Hr, Desolvation Gas Flow: 700 L/Hr, Mass range: 140 to 800 Da) and an Acquity UPLC from Waters: Binary pump, heated column compartment and diode-array detector. Solvent degasser, binary pump, heated column compartment and diode-array detector. Column: Waters UPLC HSS T3, 1.8 micron, 30×2.1 mm, Temp: 60° C., DAD Wavelength range (nm): 210 to 400, Solvent Gradient: A=water+5% MeOH+0.1% HCOOH, B=Acetonitrile+0.1% HCOOH; gradient: 0 min 100% A; 2.5 min 100% B; 2.8 min 100% B; 3.0 min 100% A; Flow (ml/min) 0.75.

BIOLOGICAL EXAMPLES

A) Reduced Plant Water Use in Soybean

Compounds were tested for their effect on reducing plant water use as follows. Each compound was dissolved in a blank emulsifiable concentrate (EC) formulation that was then diluted to the desired concentration with water containing additional surfactant (EXTRAVON 1 g/20 L). The compounds were applied by foliar spray to 12 day old soybean plants (variety S20-G7) grown in controlled environment plant growth chambers. Plant water use during the day was assessed by repeated weighing of the pots in which the plants were grown before and after application of the compounds at the indicated times (expressed in days after application (DAA)). The water use data before application was used to correct any differences in water use arising due to non-treatment effects (e.g. due to differences in plant size). The untransformed water use values were subjected to an analysis of covariance, fitting the effect of treatment and using the baseline water use 1 day before application as a covariate.

The results are expressed compared to negative control treatment (diluted EC formulation without active ingredient but with EXTRAVON 1 g/20 L).

Application of the chemicals (0 DAA) takes place approximately between 08:00 and 09:30 a.m. WU is measured within day time (chamber light is on 06:00 to 20:00) at these timepoints: 0 DAA a.m. (10:30-12:50), 0 DAA p.m. (14:00-19:50), 1 DAA a.m. (7:30-12:50), 1 DAA p.m. (14:00-19:50), 2 DAA a.m. (07:30-12:50) and 2 DAA p.m. (14:00-19:50). The cumulative total WU (0-2.5 DAA) is calculated by summing the WU data mentioned above.

TABLE B1

Percent increase or decrease of water use (WU) during day time of soybean plants sprayed with the indicated compounds at 500 µM compared to a negative control treatment (e.g. 0 = identical to negative control; −8.5 = −8.5% decrease in water use compared to negative control treatment). Average WU values of 6 pots (each with three plants) per treatment are shown.

| | % WU | | | | | | |
|---|---|---|---|---|---|---|---|
| Compounds | 0 DAA AM | 0DAA PM | 1DAA AM | 1DAA PM | 2 DAA AM | 2 DAA PM | Total 0 to 2.5 DAA |
| Untreated Control | 0 | 0 | 0 | 0 | 0 | 0 | 0 |
| 3.005 | −37.5 | −32.9 | −24.9 | −21.9 | −12.9 | −12.0 | −21.9 |
| 2.010 | −15.2 | −5.7 | −2.6 | −1.7 | −3.6 | −2.4 | −4.3 |
| 3.016 | −3.6 | −5.8 | −1.3 | −0.5 | −1.1 | 0 | −1.2 |
| 3.012 | −43.9 | −17.8 | −1.8 | 2.1 | 1.7 | 3.0 | −5.8 |
| 2.001 | −35.3 | −34.3 | −29.1 | −28.1 | −19.6 | −14.3 | −25.7 |
| 3.001 | −15.0 | −13.1 | −9.9 | −6.7 | −7.2 | −5.8 | −8.8 |
| 3.007 | −16.1 | −14.1 | −12.7 | −9.7 | −7.7 | −7.6 | −10.8 |
| 3.006 | −36.5 | −35.8 | −28.3 | −24.2 | −17.8 | −14.9 | −24.5 |

TABLE B1-continued

Percent increase or decrease of water use (WU) during day time of soybean plants sprayed with the indicated compounds at 500 μM compared to a negative control treatment (e.g. 0 = identical to negative control; −8.5 = −8.5% decrease in water use compared to negative control treatment). Average WU values of 6 pots (each with three plants) per treatment are shown.

| Compounds | % WU | | | | | | |
|---|---|---|---|---|---|---|---|
| | 0 DAA AM | 0DAA PM | 1DAA AM | 1DAA PM | 2 DAA AM | 2 DAA PM | Total 0 to 2.5 DAA |
| 3.009 | −17.5 | −14.9 | −9.4 | −6.4 | −5.5 | −4.2 | −8.5 |
| 3.011 | −3.6 | −4.0 | −3.6 | −2.3 | −3.6 | −2.4 | −3.0 |
| 3.010 | −28 | −12.5 | −3.0 | −1.0 | −2.1 | −1.7 | −5.7 |
| 2.007 | −14.1 | −9.5 | −7.3 | −6.6 | −8.8 | −5.7 | −8.1 |
| 2.009 | −5.3 | −3.0 | −2.0 | −1.2 | −3.1 | −1.0 | −2.3 |
| 2.006 | −23.4 | −17.6 | −13.8 | −13.0 | −10.4 | −7.3 | −13.2 |
| 2.014 | −2.8 | −0.7 | −0.2 | −0.9 | −0.9 | −1.7 | −1.1 |
| 3.002 | −22.5 | −20.6 | −13.7 | −9.4 | −6.7 | −4.7 | −11.4 |
| 2.002 | −10.4 | −8.5 | −6.5 | −4.0 | −5.6 | −4.2 | −5.8 |
| 2.068 | −27.0 | −22.4 | −18.1 | −14.7 | −11.6 | −7.5 | −15.3 |
| 3.068 | −46.0 | −46.5 | −39.3 | −31.6 | −22.3 | −15.3 | −31.6 |
| 3.060 | −7.9 | −4.6 | −5.8 | −2.6 | −5.4 | −2.7 | −4.6 |
| 3.063 | −9.3 | −4.7 | −5.1 | −3.9 | −6.6 | −5.0 | −5.5 |
| 3.064 | −34.7 | −29.8 | −23.3 | −21.3 | −17.2 | −13.5 | −22.2 |
| 2.061 | −50.4 | −38.6 | −7.9 | −2.2 | −0.5 | −1.2 | −13.7 |
| 3.061 | −47.8 | −22.2 | +1 | +3.4 | +1.6 | 1.2 | −13.7 |
| 3.020 | −19.3 | −12.3 | −10.1 | −5.5 | −7.4 | −4.2 | −8.5 |
| 3.067 | −28.4 | −24.3 | −19.3 | −17.2 | −13.3 | −9.5 | −17.2 |
| 3.074 | −8.6 | −3 | 0 | +1 | −1.5 | 0 | −1.4 |
| 3.075 | −10.8 | −5.8 | −2.1 | −0.6 | −2.1 | −2 | −3.3 |
| 15.001 | −27.4 | −24.2 | −14.9 | −13.9 | −9.5 | −7.2 | −15.1 |
| 15.006 | −32.6 | −32.2 | −23.6 | −24.4 | −17 | −17.8 | −23.8 |
| 17.001 | −41.6 | −43.1 | −38 | −36.3 | −27.1 | −26.3 | −34.7 |
| 20.001 | −50.1 | −54 | −58.5 | −55.2 | −55.8 | −50.5 | −54.4 |
| 3.072 | −39.4 | −42.4 | −45.9 | −40.9 | −39.8 | −32.2 | −40.1 |
| 3.073 | −44.6 | −47.9 | −54.9 | −52.1 | −53.3 | −48.7 | −51 |
| 22.001 | −46.1 | −48.5 | −55.8 | −53 | −55.1 | −50.1 | −52.1 |
| 5.001 | −15.1 | −19.2 | −18.7 | −17.4 | −16.5 | −15.6 | −17.1 |
| 5.006 | −13.6 | −13.6 | −12.5 | −11.5 | −9.7 | −9.9 | −11.4 |
| 7.001 | −17.1 | −14.1 | −9.1 | −6.9 | −6.9 | −2.5 | −8.8 |
| 7.006 | −14.6 | −12.2 | −6.7 | −4.2 | −4.2 | 0 | −6.1 |
| 7.009 | −8.1 | −7.4 | −3.6 | −3.5 | −4 | −1.7 | −4.1 |
| 10.001 | −25.2 | −27.8 | −23.8 | −22.7 | −14.9 | −14.7 | −20.8 |
| 10.006 | −22.4 | −20.3 | −18.5 | −18.2 | −16.9 | −17.8 | −18.6 |
| 11.001 | −20.8 | −24.4 | −26.2 | −27.6 | −26.9 | −26.9 | −26.1 |
| 11.006 | −13 | −14.7 | −15.3 | −15.7 | −16.4 | −16.5 | −15.8 |
| 13.001 | −15.1 | −14.3 | −11 | −11 | −8.9 | −9.2 | −11.1 |
| 13.006 | −9.8 | −10.2 | −9.3 | −10.1 | −9.6 | −10.3 | −10.1 |
| 16.001 | −39 | −44.8 | −49 | −48.1 | −45.7 | −44.5 | −46 |
| 24.001 | −35.3 | −40.3 | −42.8 | −42.8 | −39.9 | −38.3 | −40.6 |
| 23.001 | −31.3 | −36.9 | −39.7 | −40.8 | −35.9 | −37.3 | −37.7 |
| 25.001 | −28.2 | −37.2 | −41 | −39.6 | −38.1 | −36.7 | −37.9 |

The results show that soy plants treated with compounds of the present invention use less water than untreated plants.

TABLE B2

Percent increase or decrease of water use (WU) during day time of soybean plants sprayed with the indicated compounds at indicated rate compared to a negative control treatment (e.g. 0 = identical to negative control; −8.5 = −8.5% decrease in water use compared to negative control treatment). Average WU values of 6 pots (each with three plants) per treatment are shown.

| Compounds | Rate | % WU | | | | | | |
|---|---|---|---|---|---|---|---|---|
| | | 0 DAA AM* | 0DAA PM | 1DAA AM | 1DAA PM | 2 DAA AM | 2 DAA PM | Total 0 to 2.5 DAA |
| Quinabactin | | −0.3 | −0.3 | 0.2 | −0.1 | −0.9 | −1.3 | −0.7 |
| 2.001 | 31.25 uM | −0.7 | −1.4 | −1.8 | −0.9 | −2.7 | −1.5 | −1.7 |
| 3.001 | | −4.4 | −7.7 | −6.9 | −5.4 | −5.8 | −2.2 | −5.7 |
| Quinabactin | | −15.3 | −5.7 | 1.8 | 2.9 | 2.4 | 1.1 | −0.5 |
| 2.001 | 125 uM | −10.4 | −11.5 | −10.1 | −10.9 | −11.7 | −10.1 | −11.1 |
| 3.001 | | −23.7 | −23.7 | −15.7 | −15.3 | −9.3 | −6.3 | −14.8 |

TABLE B2-continued

Percent increase or decrease of water use (WU) during day time of soybean plants sprayed with the indicated compounds at indicated rate compared to a negative control treatment (e.g. 0 = identical to negative control; −8.5 = −8.5% decrease in water use compared to negative control treatment).
Average WU values of 6 pots (each with three plants) per treatment are shown.

| | | % WU | | | | | | |
|---|---|---|---|---|---|---|---|---|
| Compounds | Rate | 0 DAA AM* | 0DAA PM | 1DAA AM | 1DAA PM | 2 DAA AM | 2 DAA PM | Total 0 to 2.5 DAA |
| Quinabactin | | −42.0 | −41.2 | −18.6 | −10.8 | −3.8 | −2.9 | −16.9 |
| 2.001 | 500 uM | −41.2 | −43.4 | −36.3 | −33.2 | −24.2 | −19.5 | −31.8 |
| 3.001 | | −44.6 | −45.5 | −36.4 | −33.3 | −21.4 | −15.1 | −31.1 |

The results show that plants treated with compounds of the present invention use less water than plants treated with control compound quinabactin.

B) Reduced Plant Water Use in Corn

Compounds were tested for their effect on reducing plant water use as follows. The compounds were applied by foliar spray to 12 day old corn plants (variety NK OCTET) grown in controlled environment plant growth chambers. All compounds were applied using an emulsifiable concentrate (EC) formulation that was diluted to the desired concentrations with water containing 0.4% of the adjuvant rape seed methyl ester. Plant water use during the day was assessed by repeated weighing of the pots in which the plants were grown before and after application of the compounds at the indicated times (expressed in days after application (DAA)).

The water use data before application was used to correct any differences in water use arising due to non-treatment effects (e.g. due to differences in plant size). The untransformed water use values were subjected to an analysis of covariance, fitting the effect of treatment and using the baseline water use 1 day before application as a covariate.

Application of the chemicals (0 DAA) takes place approximately between 08:00 and 09:30 a.m. WU is measured within day time (chamber light is on 06:00 to 20:00) at these timepoints: 0 DAA a.m. (10:30-12:50), 0 DAA p.m. (14:00-19:50), 1 DAA a.m. (07:30-12:50), 1 DAA p.m. (14:00-19:50), 2 DAA a.m. (07:30-12:50) and 2 DAA p.m. (14:00-19:50). The cumulative total WU (0-2.5 DAA) is calculated by summing the WU data mentioned above.

TABLE B3

Percent increase or decrease of water use (WU) during day time of corn plants sprayed with the indicated compounds at 500 μM compared to a negative control treatment (e.g. 0 = identical to negative control; −8.5 = −8.5% decrease in water use compared to negative control treatment).
Average WU values of 6 pots (each with three plants) per treatment are shown.

| | % WU | | | | | | |
|---|---|---|---|---|---|---|---|
| Compounds | 0 DAA AM | 0DAA PM | 1DAA AM | 1DAA PM | 2 DAA AM | 2 DAA PM | Total 0 to 2.5 DAA |
| Untreated Control | 0 | 0 | 0 | 0 | 0 | 0 | 0 |
| 2.002 | −10.8 | −3.6 | −3.2 | −3.9 | −1.2 | −1.7 | −3.2 |
| 2.006 | −12.5 | −6.7 | −6.5 | −5.5 | −3.0 | −3.2 | −5.4 |
| 2.015 | −8.9 | −3.4 | −4.0 | −2.6 | −1.9 | −1.0 | −2.9 |
| 2.051 | −13.2 | −8.5 | −10.7 | −8.6 | −8.7 | −6.5 | −9.1 |
| 2.068 | −16.6 | −15.1 | −12.9 | −11.4 | −9.2 | −9.1 | −11.8 |
| 2.069 | −6.5 | −3.5 | −3.3 | −3.7 | −2.1 | −1.9 | −3.2 |
| 2.070 | −8.1 | −4.1 | −6.1 | −5.5 | −4.8 | −3.8 | −5.0 |
| 3.002 | −16.3 | −12.2 | −13.4 | −10.5 | −9.5 | −7.0 | −10.9 |
| 3.004 | −17.3 | −12.5 | −14.1 | −12.9 | −11.8 | −10.7 | −12.8 |
| 3.005 | −16.2 | −10.5 | −9.2 | −7.9 | −5.4 | −5.3 | −8.2 |
| 3.006 | −18.0 | −14.1 | −12.6 | −10.2 | −6.6 | −5.7 | −10.3 |
| 3.007 | −16.0 | −12.0 | −11.4 | −9.5 | −6.6 | −5.9 | −9.4 |
| 3.009 | −16.9 | −13.9 | −13.2 | −11.9 | −9.0 | −8.2 | −11.6 |
| 3.010 | −14.4 | −8.3 | −6.3 | −5.4 | −2.5 | −2.2 | −5.5 |
| 3.017 | −5.8 | −3.1 | −3.1 | −2.5 | −1.8 | −2.1 | −2.7 |
| 3.020 | −19.2 | −13.7 | −14.8 | −12.1 | −11.5 | −8.5 | −12.7 |
| 3.051 | −11.2 | −6.4 | −8.1 | −5.5 | −5.4 | −4.3 | −6.2 |
| 3.052 | −9.6 | −4.6 | −4.5 | −4.5 | −2.2 | −2.5 | −4.1 |
| 3.053 | −8.0 | −3.7 | −4.1 | −3.6 | −2.9 | −2.4 | −3.6 |
| 3.056 | −8.4 | −2.7 | −5.6 | −4.4 | −4.7 | −3.2 | −4.6 |
| 3.060 | −14.8 | −10.0 | −10.6 | −8.4 | −8.2 | −6.4 | −9.3 |
| 3.062 | −17.8 | −13.0 | −13.0 | −9.8 | −8.1 | −6.3 | −10.5 |
| 3.063 | −8.4 | −3.1 | −3.0 | −1.0 | −1.5 | +2 | −1.4 |
| 3.064 | −12.6 | −14.2 | −11.6 | −9.9 | −5.6 | −4.7 | −9.3 |
| 2.061 | −18.8 | −10.8 | −7.5 | −2.8 | −1.6 | −0.8 | −6.2 |
| 3.061 | −20.8 | −19.1 | −9.5 | −7.5 | −2.8 | −3.9 | −9 |
| 3.066 | −10.8 | −7.1 | −7.1 | −6.8 | −4.7 | −5.5 | −6.4 |
| 3.067 | −14.7 | −10.7 | −12.1 | −11.5 | −9.9 | −10.1 | −11.1 |
| 3.068 | −25.5 | −24.9 | −15.8 | −13.1 | −8.9 | −9.4 | −14.8 |

TABLE B3-continued

Percent increase or decrease of water use (WU) during day time of corn plants sprayed with the indicated compounds at 500 μM compared to a negative control treatment (e.g. 0 = identical to negative control; −8.5 = −8.5% decrease in water use compared to negative control treatment). Average WU values of 6 pots (each with three plants) per treatment are shown.

| Compounds | % WU | | | | | | |
|---|---|---|---|---|---|---|---|
| | 0 DAA AM | 0DAA PM | 1DAA AM | 1DAA PM | 2 DAA AM | 2 DAA PM | Total 0 to 2.5 DAA |
| 3.069 | −8.1 | −4.1 | −6.1 | −5.5 | −4.8 | −3.8 | −5.0 |
| 3.071 | −11.2 | −6.5 | −4.5 | −4.7 | −3.5 | −2.4 | −4.9 |
| 3.075 | −9.8 | −7.9 | −8.2 | −6.4 | −4.9 | −3.3 | −6.3 |
| 15.001 | −8.2 | −6.5 | −6.5 | −3.5 | −2.8 | −1.8 | −4.3 |
| 15.006 | −10.2 | −3 | −1.4 | 0.1 | 1.7 | 1.1 | −1.2 |
| 15.009 | −10.7 | −7.8 | −8.7 | −5.8 | −5.4 | −5.7 | −7.1 |
| 20.001 | −21.7 | −18.3 | −19.2 | −10.3 | −8.1 | −5.5 | −12.9 |
| 20.006 | −15.5 | −14.5 | −13.2 | −7 | −5.7 | −4.3 | −9.4 |

The results show that corn plants treated with compounds of the present invention use less water than untreated plants.

The invention claimed is:
1. A compound of formula (I)

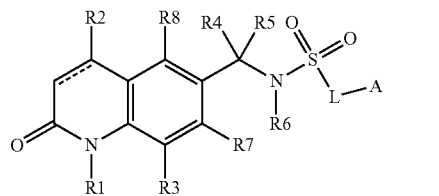

wherein:
R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$alkenyl, $C_3$-$C_7$ alkynyl, (3-6 membered heterocycloalkyl)-$C_1$-$C_7$ alkyl, $C_3$-$C_5$ cycloalkyl and a 4-6 membered heterocycloalkyl, each optionally substituted with one to three Rx;
R2 is selected from the group consisting of hydrogen, cyano, $C_1$-$C_4$ alkyl, $C_1$-$C_4$ alkoxy, $C_1$-$C_4$ haloalkyl, $C_1$-$C_4$haloalkoxy and $C_3$-$C_4$ cycloalkyl;
R3, R7 and R8 are independently selected from the group consisting of hydrogen, halogen, cyano, $C_1$-$C_4$alkyl, $C_2$-$C_4$ alkenyl, $C_2$-$C_4$ alkynyl, $C_1$-$C_4$ alkoxy, $C_1$-$C_4$haloalkyl, $C_1$-$C_4$ haloalkoxy and $C_3$-$C_4$ cycloalkyl;
R4 and R5 are independently selected from the group consisting of hydrogen, $C_1$-$C_4$ alkyl, $C_1$-$C_4$ haloalkyl and $C_3$-$C_4$ cycloalkyl;
or R4 and R5 can form, together with the atom or atoms they are directly attached to, a $C_3$-$C_4$ cycloalkyl or $C_4$heterocyclyl;
R6 is selected from the group consisting of hydrogen, $C_1$-$C_4$ alkyl, $C_3$-$C_4$ alkenyl, $C_3$-$C_4$ alkynyl, and $C_1$-$C_3$alkoxy-$C_1$-$C_4$-alkyl;
L is selected from the group consisting of a bond, a linear —$C_1$-$C_4$-alkyl chain, a linear —$C_2$-$C_4$-alkenyl chain, a linear —$C_2$-$C_4$-alkynyl chain, a linear —$C_1$-$C_4$-alkoxy chain whereby the oxygen atom is attached to A, a linear -amino-$C_1$-$C_4$-alkyl-chain whereby the nitrogen atom is attached to A, and a linear $C_1$-$C_2$alkyl-oxy-$C_1$-$C_2$alkyl, chain each optionally substituted with one to three halogen, cyano, $C_1$-$C_4$ alkyl, $C_1$-$C_4$ haloalkyl or $C_1$-$C_4$ alkoxy;
A is hydrogen, $C_1$-$C_7$ alkyl, $C_3$-$C_5$ cycloalkyl, 3-10 membered heterocyclyl or aryl, each optionally substituted with one to three Ry;
Rx is, independently of each other, selected from the group consisting of halogen, cyano, $C_1$-$C_4$ alkyl, $C_1$-$C_4$haloalkyl, $C_1$-$C_4$ alkoxy, $C_1$-$C_4$ haloalkoxy, $C_1$-$C_4$alkylcarbonyl, $C_1$-$C_4$ alkoxycarbonyl, carboxylic acid, aminocarbonyl, $C_1$-$C_4$ aminocarbonyl and $C_3$-$C_4$cycloalkyl;
Ry is, independently of each other, selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkyloxy, $C_1$-$C_4$alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$haloalkylsulfonyl, $C_1$-$C_4$ alkylcarbonyl, $C_1$-$C_4$alkoxycarbonyl, carboxylic acid, aminocarbonyl, $C_1$-$C_4$aminocarbonyl and $C_3$-$C_4$ cycloalkyl which cycloalkyl is unsubstituted or substituted by one or more Rz;
Rz is independently selected from the group consisting of halogen, $C_1$-$C_4$-alkyl and $C_1$-$C_4$-haloalkyl;
wherein A is not butyl when either R4 or R5 is methyl;
and wherein R1 is not methyl when R2, R3, R4, R5, R6, R7 and R8 are each hydrogen;
or salts or N-oxides thereof.

2. The compound of claim 1, wherein R1 is selected from the group consisting of $C_1$-$C_6$ alkyl, $C_1$-$C_6$haloalkyl, $C_3$-$C_6$ alkenyl and $C_3$-$C_5$ cyclopropyl-$C_1$-$C_6$-alkyl.

3. The compound of claim 2, wherein R1 is ethyl or propyl.

4. The compound of claim 1, wherein L is a bond.

5. The compound of claim 1, wherein A is selected from the group consisting of $C_1$-$C_7$ alkyl, phenyl and 3-6 membered heteroaryl, each optionally substituted with one to three Ry.

6. The compound of claim 5, wherein A is phenyl optionally substituted with one to three substituents independently selected from the group consisting of halogen, $C_1$-$C_4$ haloalkyl, $C_1$-$C_4$ alkyl and $C_1$-$C_4$haloalkoxy.

7. The compound of claim 1, wherein R2 is selected from the group consisting of hydrogen and $C_1$-$C_4$ alkyl.

8. The compound of claim 1, wherein R3 is selected from the group consisting of hydrogen, halogen and $C_1$-$C_4$ alkyl.

9. The compound of claim 1, wherein R2, R3, R4, R5, R6, R7 and R8 are hydrogen.

10. A composition, comprising:
a compound according to claim 1; and
an agriculturally acceptable formulation adjuvant.

11. A composition, comprising
a compound as defined in claim 1; and
an agriculturally active ingredient selected from acaricides, bactericides, fungicides, herbicides, insecticides, nematicides, plant growth regulators, crop enhancing agents, safeners, plant nutrients and plant fertilizers.

12. A method for at least one of improving the tolerance of a plant to abiotic stress, regulating the growth of a plant, or improving the growth of a plant, wherein the method comprises applying to the plant, plant part, plant propagation material, or plant growing locus a compound according to claim 1.

13. A method for inhibiting seed germination of a plant, wherein the method comprises applying to the plant, plant part, plant propagation material or plant growing locus a compound according claim 1.

14. A method for at least one of improving the tolerance of a plant to abiotic stress, regulating the growth of a plant, or improving the growth of a plant, wherein the method comprises applying to the plant, plant part, plant propagation material, or plant growing locus a compound of formula (I)

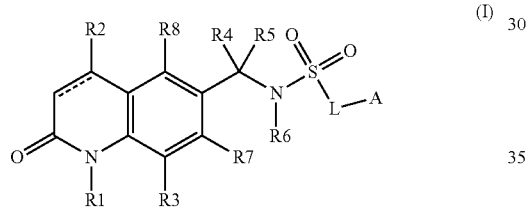

wherein:
R1 is selected from the group consisting of $C_1$-$C_7$ alkyl, $C_1$-$C_7$ haloalkyl, $C_3$-$C_5$ cycloalkyl-$C_1$-$C_7$ alkyl, $C_3$-$C_7$alkenyl, $C_3$-$C_7$ alkynyl, aryl-$C_1$-$C_7$ alkyl, (3-6 membered heterocyclyl)-$C_1$-$C_7$ alkyl, phenyl, $C_3$-$C_5$ cycloalkyl and a 4-6 membered heterocyclyl, each optionally substituted with one to three Rx;
R2 is selected from the group consisting of hydrogen, cyano, $C_1$-$C_4$ alkyl, $C_1$-$C_4$ alkoxy, $C_1$-$C_4$ haloalkyl, $C_1$-$C_4$haloalkoxy and $C_3$-$C_4$ cycloalkyl;
R3, R7 and R8 are independently selected from the group consisting of hydrogen, halogen, cyano, $C_1$-$C_4$alkyl, $C_2$-$C_4$ alkenyl, $C_2$-$C_4$ alkynyl, $C_1$-$C_4$ alkoxy, $C_1$-$C_4$haloalkyl, $C_1$-$C_4$ haloalkoxy and $C_3$-$C_4$ cycloalkyl;
R4 and R5 are independently selected from the group consisting of hydrogen, $C_1$-$C_4$ alkyl, $C_1$-$C_4$ haloalkyl and $C_3$-$C_4$ cycloalkyl;
or R4 and R5 can form, together with the atom or atoms they are directly attached to, a $C_3$-$C_4$ cycloalkyl or $C_4$heterocyclyl;
R6 is selected from the group consisting of hydrogen, $C_1$-$C_4$ alkyl, $C_3$-$C_4$ alkenyl, $C_3$-$C_4$ alkynyl, and $C_1$-$C_3$alkoxy-$C_1$-$C_4$-alkyl;
L is selected from the group consisting of a bond, a linear —$C_1$-$C_4$-alkyl chain, a linear —$C_2$-$C_4$-alkenyl chain, a linear —$C_2$-$C_4$-alkynyl chain, a linear —$C_1$-$C_4$-alkoxy chain whereby the oxygen atom is attached to A, a linear -amino-$C_1$-$C_4$-alkyl-chain whereby the nitrogen atom is attached to A, and a linear $C_1$-$C_2$alkyl-oxy-$C_1$-$C_2$alkyl, chain each optionally substituted with one to three halogen, cyano, $C_1$-$C_4$ alkyl, $C_1$-$C_4$ haloalkyl or $C_1$-$C_4$ alkoxy;
A is hydrogen, $C_1$-$C_7$ alkyl, $C_3$-$C_5$ cycloalkyl, 3-10 membered heterocyclyl or aryl, each optionally substituted with one to three Ry;
Rx is, independently of each other, selected from the group consisting of halogen, cyano, $C_1$-$C_4$ alkyl, $C_1$-$C_4$haloalkyl, $C_1$-$C_4$ alkoxy, $C_1$-$C_4$ haloalkoxy, $C_1$-$C_4$alkylcarbonyl, $C_1$-$C_4$ alkoxycarbonyl, carboxylic acid, aminocarbonyl, $C_1$-$C_4$ aminocarbonyl and $C_3$-$C_4$cycloalkyl;
Ry is, independently of each other, selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkyloxy, $C_1$-$C_4$alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$haloalkylsulfonyl, $C_1$-$C_4$ alkylcarbonyl, $C_1$-$C_4$alkoxycarbonyl, carboxylic acid, aminocarbonyl, $C_1$-$C_4$aminocarbonyl and $C_3$-$C_4$ cycloalkyl which cycloalkyl is unsubstituted or substituted by one or more Rz;
Rz is independently selected from the group consisting of halogen, $C_1$-$C_4$-alkyl and $C_1$-$C_4$-haloalkyl;
wherein A is not butyl when either R4 or R5 is methyl;
and wherein R1 is not methyl when R2, R3, R4, R5, R6, R7 and R8 are each hydrogen;
or salts or N-oxides thereof.

15. A method for inhibiting seed germination of a plant, wherein the method comprises applying to the plant, plant part, plant propagation material or plant growing locus a compound of formula (I)

wherein:
R1 is selected from the group consisting of $C_1$-$C_7$ alkyl, $C_1$-$C_7$ haloalkyl, $C_3$-$C_5$ cycloalkyl $C_1$-$C_7$ alkyl, $C_3$-$C_7$alkenyl, $C_3$-$C_7$ alkynyl, aryl-$C_1$-$C_7$ alkyl, (3-6 membered heterocyclyl)-$C_1$-$C_7$ alkyl, phenyl, $C_3$-$C_5$ cycloalkyl and a 4-6 membered heterocyclyl, each optionally substituted with one to three Rx;
R2 is selected from the group consisting of hydrogen, cyano, $C_1$-$C_4$ alkyl, $C_1$-$C_4$ alkoxy, $C_4$ haloalkyl, $C_1$-$C_4$haloalkoxy and $C_3$-$C_4$ cycloalkyl;
R3, R7 and R8 are independently selected from the group consisting of hydrogen, halogen, cyano, $C_1$-$C_4$alkyl, $C_2$-$C_4$ alkenyl, $C_2$-$C_4$ alkynyl, $C_1$-$C_4$ alkoxy, $C_1$-$C_4$haloalkyl, $C_1$-$C_4$ haloalkoxy and $C_3$-$C_4$ cycloalkyl;
R4 and R5 are independently selected from the group consisting of hydrogen, $C_1$-$C_4$ alkyl, $C_1$-$C_4$ haloalkyl and $C_3$-$C_4$ cycloalkyl;
or R4 and R5 can form, together with the atom or atoms they are directly attached to, a $C_3$-$C_4$ cycloalkyl or $C_4$heterocyclyl;

R6 is selected from the group consisting of hydrogen, $C_1$-$C_4$ alkyl, $C_3$-$C_4$ alkenyl, $C_3$-$C_4$ alkynyl, and $C_1$-$C_3$alkoxy-$C_1$-$C_4$-alkyl;

L is selected from the group consisting of a bond, a linear —$C_1$-$C_4$-alkyl chain, a linear —$C_2$-$C_4$-alkenyl chain, a linear —$C_2$-$C_4$-alkynyl chain, a linear —$C_1$-$C_4$-alkoxy chain whereby the oxygen atom is attached to A, a linear -amino-$C_1$-$C_4$-alkyl-chain whereby the nitrogen atom is attached to A, and a linear $C_1$-$C_2$alkyl-oxy-$C_1$-$C_2$alkyl, chain each optionally substituted with one to three halogen, cyano, $C_1$-$C_4$ alkyl, $C_1$-$C_4$ haloalkyl or $C_1$-$C_4$ alkoxy;

A is hydrogen, $C_1$-$C_7$ alkyl, $C_3$-$C_5$ cycloalkyl, 3-10 membered heterocyclyl or aryl, each optionally substituted with one to three Ry;

Rx is, independently of each other, selected from the group consisting of halogen, cyano, $C_1$-$C_4$ alkyl, $C_1$-$C_4$haloalkyl, $C_1$-$C_4$ alkoxy, $C_1$-$C_4$ haloalkoxy, $C_1$-$C_4$alkylcarbonyl, $C_1$-$C_4$ alkoxycarbonyl, carboxylic acid, aminocarbonyl, $C_1$-$C_4$ aminocarbonyl and $C_3$-$C_4$cycloalkyl;

Ry is, independently of each other, selected from the group consisting of halogen, cyano, nitro, $C_1$-$C_4$ alkyl, $C_1$-$C_4$ alkoxy, $C_1$-$C_4$ haloalkyl, $C_1$-$C_4$ haloalkyloxy, $C_1$-$C_4$alkylsulfanyl, $C_1$-$C_4$ haloalkylsulfanyl, $C_1$-$C_4$ alkylsulfinyl, $C_1$-$C_4$ haloalkylsulfinyl, $C_1$-$C_4$ alkylsulfonyl, $C_1$-$C_4$haloalkylsulfonyl, $C_1$-$C_4$ alkylcarbonyl, $C_1$-$C_4$alkoxycarbonyl, carboxylic acid, aminocarbonyl, $C_1$-$C_4$aminocarbonyl and $C_3$-$C_4$ cycloalkyl which cycloalkyl is unsubstituted or substituted by one or more Rz;

Rz is independently selected from the group consisting of halogen, $C_1$-$C_4$-alkyl and $C_1$-$C_4$-haloalkyl;

wherein A is not butyl when either R4 or R5 is methyl;

and wherein R1 is not methyl when R2, R3, R4, R5, R6, R7 and R8 are each hydrogen;

or salts or N-oxides thereof.

* * * * *